(12) United States Patent
Sakakibara et al.

(10) Patent No.: US 7,186,886 B2
(45) Date of Patent: Mar. 6, 2007

(54) ALIPHATIC ACYL TRANSFERASE GENES

(75) Inventors: Keiko Sakakibara, Wako (JP); Toru Nakayama, Sendai (JP); Tokuzo Nishino, Sendai (JP)

(73) Assignee: International Flower Developments Proprietary Limited, Victoria (AU)

( * ) Notice: Subject to any disclaimer, the term of this patent is extended or adjusted under 35 U.S.C. 154(b) by 374 days.

(21) Appl. No.: 10/048,897

(22) PCT Filed: Jun. 1, 2001

(86) PCT No.: PCT/JP01/04677

§ 371 (c)(1), (2), (4) Date: Jul. 2, 2002

(87) PCT Pub. No.: WO01/92536

PCT Pub. Date: Dec. 6, 2001

(65) Prior Publication Data

US 2004/0132016 A1    Jul. 8, 2004

(30) Foreign Application Priority Data

Jun. 2, 2000 (JP) .......................... 2000-170435
Feb. 9, 2001 (JP) .......................... 2001-34467

(51) Int. Cl.
- C12N 15/29 (2006.01)
- C12N 15/54 (2006.01)
- C12N 15/82 (2006.01)
- A01H 5/00 (2006.01)
- A01H 5/02 (2006.01)
- A01H 5/10 (2006.01)

(52) U.S. Cl. ............ 800/282; 800/298; 536/23.1; 536/23.2; 536/23.6; 435/320.1; 435/419

(58) Field of Classification Search ............ 536/23.1, 536/23.2, 23.6; 800/278, 282, 298, 323; 435/183, 193, 320.1, 419

See application file for complete search history.

(56) References Cited

FOREIGN PATENT DOCUMENTS

| WO | WO 96/25500 | 8/1996 |
|----|-------------|--------|
| WO | WO 99/05287 | 2/1999 |

OTHER PUBLICATIONS

Callebaut A. et al. Plant Science, 1996, vol. 118; pp. 109-118.*
Tanaka Y. et al. Plant Cell Physiology, 1996; vol. 37, No. 5; pp. 711-716.*
Su V. et al. Biotechnology Letters, 2000; vol. 25, pp. 1933-1939.*
Mori S. et al. Plant Cell Reports; 2004, vol. 22, pp. 415-421.*
Broun P. et al. Science vol. 282; Nov. 13, 1998, pp. 1315-1317.*
Guo H. et al. PNAS; Jun. 22, 2004, vol. 101, No. 25, pp. 9205-9210.*
Callebaut et al. Plant Science; 1996, vol. 118, pp. 109-118.*
Ishikawa T. et al., "An Acetylated Anthocyanin from the Blue Petals of Salvia Uliginosa", *Phytochemistry 52*(3): 517-521 (1999).
Alfons Callebaut, et al., "Anthocyanin acyltransferases in cell cultures of *Ajuga reptans*", Plant Science, vol. 118, No. 2, 1996, pp. 109-118.
Hiroyuki Fujiwara, et al., "cDNA cloning, gene expression and subcellular localization of anthocyanin 5-aromatic acyltransferase from *Gentiana triflora*", The Plant Journal, vol. 16, No. 4, Nov. 1998, pp. 421-431.
Vangipuram S. Rangan, et al., "Characterization of the malonyl-/acetyltransacylase domain of the multifunctional animal fatty acid synthase by expression in *Escherichia coli* and refolding in vitro", Protein Engineering, vol. 10, No. 5, 1997, pp. 561-566.
Hirokazu Suzuki, et al., "Malonyl-CoA:Anthocyanin 5-0-Glucoside-6"-0-Malonyltransferase from Scarlet Sage (*Salvia splendens*) Flowers. Enzyme purification, gene cloning, expression, and characterization, Journal of Biological Chemistry, vol. 276, No. 52, Dec. 28, 2001, pp. 49013-49019.
Mami Yamazaki, et al., "Molecular Cloning and Biochemical Characterization of a Novel Anthocyanin 5-0-Glucosyltransferase by mRNA Differential Display for Plant Forms Regarding Anthocyanin", Journal of Biological Chemistry, American Society of Biological Chemists, Baltimore, MD, vol. 274, No. 11, Mar. 12, 1999, pp. 7405-7411.
Yonekura-Sakakibara et al., "*Molecular and Biochemical Characterization of a Novel Hydroxycinnamoyl-CoA: Anthocyanin 3-O -Glucoside-6"-O-Acyltransferase from Perilla frutescens. Plant Cell Physiol*. 41(4): (2000) 495-502.

* cited by examiner

*Primary Examiner*—Russell P. Kallis
(74) *Attorney, Agent, or Firm*—Scully, Scott, Murphy & Presser, P.C.

(57) ABSTRACT

A protein which has an amino acid sequence shown by SEQ ID NO: 2, 4, 6, 23, 25, 27 or 29, or any of these amino acid sequences modified, and which has activity for transferring an aliphatic acyl group to a glycosyl group at the 5-position of flavonoids, and a gene encoding the same.

9 Claims, No Drawings

SEQUENCE LISTING

<160> NUMBER OF SEQ ID NOS: 32

<210> SEQ ID NO 1
<211> LENGTH: 1419
<212> TYPE: DNA
<213> ORGANISM: Salvia guaranitica
<220> FEATURE:
<221> NAME/KEY: CDS
<222> LOCATION: (3)..(1337)

<400> SEQUENCE: 1

```
ca aca aca aca ctc ctc gaa aca tgc cac att ccg ccg ccg ccg ccg         47
   Thr Thr Thr Leu Leu Glu Thr Cys His Ile Pro Pro Pro Pro Pro
    1               5                  10                  15 gcc aac gac ctc tca atc ccc ctc tcc ttc ttc gac atc aaa tgg ctc         95
Ala Asn Asp Leu Ser Ile Pro Leu Ser Phe Phe Asp Ile Lys Trp Leu
                 20                  25                  30 cac tac cac ccc gtc cgc cgc ctc ctc ttc tac cac cac cct tcc tcc        143
His Tyr His Pro Val Arg Arg Leu Leu Phe Tyr His His Pro Ser Ser
             35                  40                  45 aaa tcc caa ttc ctc cac aca atc gtc cca cac ctc aaa caa tca ctc        191
Lys Ser Gln Phe Leu His Thr Ile Val Pro His Leu Lys Gln Ser Leu
         50                  55                  60 tct ctc gct ctc aca cac tac ttc ccc gtc gcc ggc aac ctc ctc tac        239
Ser Leu Ala Leu Thr His Tyr Phe Pro Val Ala Gly Asn Leu Leu Tyr
 65                  70                  75 ccg tcc aac ccc gaa aaa ttc ccc caa ctc cgc tat gcc gcc ggg gat        287
Pro Ser Asn Pro Glu Lys Phe Pro Gln Leu Arg Tyr Ala Ala Gly Asp
 80                  85                  90                  95 tcc gtc ccg gtg acg atc gcg gag tcc aat tcc gac ttc gaa agc ctc        335
Ser Val Pro Val Thr Ile Ala Glu Ser Asn Ser Asp Phe Glu Ser Leu
                100                 105                 110 acc gga aac cac acg cgc gac gcc gat caa ttc tac gat ctc ctc ccg        383
Thr Gly Asn His Thr Arg Asp Ala Asp Gln Phe Tyr Asp Leu Leu Pro
            115                 120                 125 cct att cct ccg att gag gag gaa tcg gat tgg aaa ttg atc aac att        431
Pro Ile Pro Pro Ile Glu Glu Glu Ser Asp Trp Lys Leu Ile Asn Ile
        130                 135                 140
```

```
ttc gcg gtt cag atc act cta ttc ccc ggc gaa gga atc tgt gtc ggt    479
Phe Ala Val Gln Ile Thr Leu Phe Pro Gly Glu Gly Ile Cys Val Gly
    145                 150                 155 ttc tcc aat cac cac tgc ctc ggc gac gcc aga tct atc gtc gga ttc    527
Phe Ser Asn His His Cys Leu Gly Asp Ala Arg Ser Ile Val Gly Phe
160                 165                 170                 175 atc tcc gct tgg ggt gaa atc aac gga atc gga gga tat gaa gga ttc    575
Ile Ser Ala Trp Gly Glu Ile Asn Gly Ile Gly Gly Tyr Glu Gly Phe
                180                 185                 190 tta tcc aat cgc agt gat tct ctc tcc ctt ccg att ttc gat cga tcg    623
Leu Ser Asn Arg Ser Asp Ser Leu Ser Leu Pro Ile Phe Asp Arg Ser
            195                 200                 205 ttt att aac gat ccg aac aaa atc gac gct att ttc tgg aaa gtg atg    671
Phe Ile Asn Asp Pro Asn Lys Ile Asp Ala Ile Phe Trp Lys Val Met
        210                 215                 220 aga aac ata cct ttg aaa acg gcg tcg ttt ccg ctg cct acg aac aga    719
Arg Asn Ile Pro Leu Lys Thr Ala Ser Phe Pro Leu Pro Thr Asn Arg
    225                 230                 235 gtc aga tct aca ttc ctc ctc cgc aga tcc gac atc gag aag ctg aaa    767
Val Arg Ser Thr Phe Leu Leu Arg Arg Ser Asp Ile Glu Lys Leu Lys
240                 245                 250                 255 acc gcc acc aaa tcg ccg gcg tcg tcg ttc gtc gct gca gca gcg ttc    815
Thr Ala Thr Lys Ser Pro Ala Ser Ser Phe Val Ala Ala Ala Ala Phe
                260                 265                 270 gtc tgg agc tgt atg gtg aaa tcc ggc gac aaa tcc aac gaa aat gcg    863
Val Trp Ser Cys Met Val Lys Ser Gly Asp Lys Ser Asn Glu Asn Ala
            275                 280                 285 ccg gag ctt ttc atc ata cct gcg gac gcc agg ggg agg att gat ccg    911
Pro Glu Leu Phe Ile Ile Pro Ala Asp Ala Arg Gly Arg Ile Asp Pro
        290                 295                 300 ccg ata ccg gag aat tac ttc ggc aac tgc atc gtg agc tcg gtg gcg    959
Pro Ile Pro Glu Asn Tyr Phe Gly Asn Cys Ile Val Ser Ser Val Ala
    305                 310                 315 cgg gtg gag cgc ggg aag ctg ctg gcg gag gac gga ttc gcg gcg gcg   1007
Arg Val Glu Arg Gly Lys Leu Leu Ala Glu Asp Gly Phe Ala Ala Ala
320                 325                 330                 335 gct gaa gca att agc ggg gag atc gag ggg aaa ttg aaa aac aga gat   1055
Ala Glu Ala Ile Ser Gly Glu Ile Glu Gly Lys Leu Lys Asn Arg Asp
                340                 345                 350 gag att ttg aga gga gcg gag aat tgg atg tcg gac ata ttc aaa tgc   1103
Glu Ile Leu Arg Gly Ala Glu Asn Trp Met Ser Asp Ile Phe Lys Cys
            355                 360                 365 ttc ggg atg agc gtg ctc gga gtt tct gga tcg ccg aaa ttc gat ctg   1151
Phe Gly Met Ser Val Leu Gly Val Ser Gly Ser Pro Lys Phe Asp Leu
        370                 375                 380 ttg aag gcg gat ttt gga tgg gga aag gcg agg aaa ttg gag gtg ctg   1199
Leu Lys Ala Asp Phe Gly Trp Gly Lys Ala Arg Lys Leu Glu Val Leu
    385                 390                 395 tcg att gat gga gag aat cac tca atg tcg ctg tgt agc tcg agc gat   1247
Ser Ile Asp Gly Glu Asn His Ser Met Ser Leu Cys Ser Ser Ser Asp
400                 405                 410                 415 ttc aat ggc gga ttg gag gtg ggt ttg tca ttg cct aga gag aga atg   1295
Phe Asn Gly Gly Leu Glu Val Gly Leu Ser Leu Pro Arg Glu Arg Met
                420                 425                 430 gcg gca ttt gca gag gtg ttt act gat gga ctt gcc aat ctt            1337
Ala Ala Phe Ala Glu Val Phe Thr Asp Gly Leu Ala Asn Leu
            435                 440                 445 tgaataattt tcattttata gttattaatt aaatatctta catccaatag taatatctta   1397
```

-continued attatattcg atattccttc at 1419

<210> SEQ ID NO 2
<211> LENGTH: 445
<212> TYPE: PRT
<213> ORGANISM: Salvia guaranitica

<400> SEQUENCE: 2

```
Thr Thr Thr Leu Leu Glu Thr Cys His Ile Pro Pro Pro Pro Ala
 1               5                  10                  15

Asn Asp Leu Ser Ile Pro Leu Ser Phe Phe Asp Ile Lys Trp Leu His
             20                  25                  30

Tyr His Pro Val Arg Arg Leu Leu Phe Tyr His His Pro Ser Ser Lys
         35                  40                  45

Ser Gln Phe Leu His Thr Ile Val Pro His Leu Lys Gln Ser Leu Ser
     50                  55                  60

Leu Ala Leu Thr His Tyr Phe Pro Val Ala Gly Asn Leu Leu Tyr Pro
 65                  70                  75                  80

Ser Asn Pro Glu Lys Phe Pro Gln Leu Arg Tyr Ala Ala Gly Asp Ser
                 85                  90                  95

Val Pro Val Thr Ile Ala Glu Ser Asn Ser Asp Phe Glu Ser Leu Thr
            100                 105                 110

Gly Asn His Thr Arg Asp Ala Asp Gln Phe Tyr Asp Leu Leu Pro Pro
        115                 120                 125

Ile Pro Pro Ile Glu Glu Glu Ser Asp Trp Lys Leu Ile Asn Ile Phe
    130                 135                 140

Ala Val Gln Ile Thr Leu Phe Pro Gly Glu Gly Ile Cys Val Gly Phe
145                 150                 155                 160

Ser Asn His His Cys Leu Gly Asp Ala Arg Ser Ile Val Gly Phe Ile
                165                 170                 175

Ser Ala Trp Gly Glu Ile Asn Gly Ile Gly Gly Tyr Glu Gly Phe Leu
            180                 185                 190

Ser Asn Arg Ser Asp Ser Leu Ser Leu Pro Ile Phe Asp Arg Ser Phe
        195                 200                 205

Ile Asn Asp Pro Asn Lys Ile Asp Ala Ile Phe Trp Lys Val Met Arg
    210                 215                 220

Asn Ile Pro Leu Lys Thr Ala Ser Phe Pro Leu Pro Thr Asn Arg Val
225                 230                 235                 240

Arg Ser Thr Phe Leu Leu Arg Arg Ser Asp Ile Glu Lys Leu Lys Thr
                245                 250                 255

Ala Thr Lys Ser Pro Ala Ser Ser Phe Val Ala Ala Ala Phe Val
            260                 265                 270

Trp Ser Cys Met Val Lys Ser Gly Asp Lys Ser Asn Glu Asn Ala Pro
        275                 280                 285

Glu Leu Phe Ile Ile Pro Ala Asp Ala Arg Gly Arg Ile Asp Pro Pro
    290                 295                 300

Ile Pro Glu Asn Tyr Phe Gly Asn Cys Ile Val Ser Ser Val Ala Arg
305                 310                 315                 320

Val Glu Arg Gly Lys Leu Leu Ala Glu Asp Gly Phe Ala Ala Ala Ala
                325                 330                 335

Glu Ala Ile Ser Gly Glu Ile Glu Gly Lys Leu Lys Asn Arg Asp Glu
            340                 345                 350

Ile Leu Arg Gly Ala Glu Asn Trp Met Ser Asp Ile Phe Lys Cys Phe
        355                 360                 365
```

```
            Gly Met Ser Val Leu Gly Val Ser Gly Ser Pro Lys Phe Asp Leu Leu
                370                 375                 380

Lys Ala Asp Phe Gly Trp Gly Lys Ala Arg Lys Leu Glu Val Leu Ser
            385                 390                 395                 400

Ile Asp Gly Glu Asn His Ser Met Ser Leu Cys Ser Ser Asp Phe
                            405                 410                 415

Asn Gly Gly Leu Glu Val Gly Leu Ser Leu Pro Arg Glu Arg Met Ala
                        420                 425                 430

Ala Phe Ala Glu Val Phe Thr Asp Gly Leu Ala Asn Leu
                        435                 440                 445

<210> SEQ ID NO 3
<211> LENGTH: 1471
<212> TYPE: DNA
<213> ORGANISM: Salvia guaranitica
<220> FEATURE:
<221> NAME/KEY: CDS
<222> LOCATION: (3)..(1322)

<400> SEQUENCE: 3 ca aca aca ctc ctc gaa aca tgc cac att ccg ccg ccg ccg gcc           47
   Thr Thr Leu Leu Glu Thr Cys His Ile Pro Pro Pro Pro Ala
    1               5                  10                  15 aac gac ctc tca atc ccc ctc tcc ttc ttc gac atc aaa tgg ctc cac     95
Asn Asp Leu Ser Ile Pro Leu Ser Phe Phe Asp Ile Lys Trp Leu His
                20                  25                  30 tac cac ccc gtc cgc cgc ctc ctc ttc tac cac cac cct tcc tcc aaa    143
Tyr His Pro Val Arg Arg Leu Leu Phe Tyr His His Pro Ser Ser Lys
            35                  40                  45 tcc caa ttc ctc cac aca atc gtt cca cac ctc aaa caa tca ctc tct    191
Ser Gln Phe Leu His Thr Ile Val Pro His Leu Lys Gln Ser Leu Ser
        50                  55                  60 ctc gct ctc aca cac tac ctc ccc gtc gcc ggc aac ctc ctc tac ccg    239
Leu Ala Leu Thr His Tyr Leu Pro Val Ala Gly Asn Leu Leu Tyr Pro
    65                  70                  75 tcc aac ccc gaa aaa ttt ccc caa ctc cgc tat gcc gcc agg gat tcc    287
Ser Asn Pro Glu Lys Phe Pro Gln Leu Arg Tyr Ala Ala Arg Asp Ser
 80                  85                  90                  95 gtc ccg gtg acg atc gcg gag tcc aat tcc gac ttc gaa agc ctc acc    335
Val Pro Val Thr Ile Ala Glu Ser Asn Ser Asp Phe Glu Ser Leu Thr
                100                 105                 110 gga aac cac acg cgc gac gcc gat caa ttc tac gat ctc ctc ccg cct    383
Gly Asn His Thr Arg Asp Ala Asp Gln Phe Tyr Asp Leu Leu Pro Pro
            115                 120                 125 att cct ccg att gag gag gaa tcg gat tgg aaa ttg atc aac att ttc    431
Ile Pro Pro Ile Glu Glu Glu Ser Asp Trp Lys Leu Ile Asn Ile Phe
        130                 135                 140 gcg gtt cag atc act cta ttc ccc ggc gaa gga atc tgc gtc ggt ttc    479
Ala Val Gln Ile Thr Leu Phe Pro Gly Glu Gly Ile Cys Val Gly Phe
    145                 150                 155 tcc aat cac cac tgc ctc ggc gac gcc aga tct atg gtc gga ttc atc    527
Ser Asn His His Cys Leu Gly Asp Ala Arg Ser Met Val Gly Phe Ile
160                 165                 170                 175 tcc gct tgg ggt gaa atc aac gga atc gga gga tat gaa gga ttc tta    575
Ser Ala Trp Gly Glu Ile Asn Gly Ile Gly Gly Tyr Glu Gly Phe Leu
                180                 185                 190 tcc aat cac agt gat tct ctc tcc ctt ccg att ttc gat cga tcg ttt    623
Ser Asn His Ser Asp Ser Leu Ser Leu Pro Ile Phe Asp Arg Ser Phe
            195                 200                 205 att aac gat ccg aac aaa atc gac gct att ttc tgg aaa gtg atg aga    671
```

```
                                                                               -continued Ile Asn Asp Pro Asn Lys Ile Asp Ala Ile Phe Trp Lys Val Met Arg
        210                 215                 220 aac ata cct ttg aaa acg gcg tcg ttt ccg ctg cct acg aac aga gtc        719
Asn Ile Pro Leu Lys Thr Ala Ser Phe Pro Leu Pro Thr Asn Arg Val
    225                 230                 235 aga tct aca ttc ctc ctc cgc aga tcc gac atc gag aag ctg aaa acc        767
Arg Ser Thr Phe Leu Leu Arg Arg Ser Asp Ile Glu Lys Leu Lys Thr
240                 245                 250                 255 gcc acc aaa tcg ccg gcg tcg tcg ttc gtc gcg gca gca gcg ttc gtc        815
Ala Thr Lys Ser Pro Ala Ser Ser Phe Val Ala Ala Ala Ala Phe Val
                260                 265                 270 tgg agc tgt atg gtg aaa tcc ggc gac aaa tcc gac gaa aat gcg ccg        863
Trp Ser Cys Met Val Lys Ser Gly Asp Lys Ser Asp Glu Asn Ala Pro
            275                 280                 285 gag ctt ttc atc ata cct gcg gac gcc agg ggg agg att gat ccg ccg        911
Glu Leu Phe Ile Ile Pro Ala Asp Ala Arg Gly Arg Ile Asp Pro Pro
        290                 295                 300 ata ccg gag aat tac ttc ggc aac tgc atc gtg agc tcg gtg gcg cgg        959
Ile Pro Glu Asn Tyr Phe Gly Asn Cys Ile Val Ser Ser Val Ala Arg
    305                 310                 315 gtg gag cgc ggg aag ctg ctg gcg gag gac gga ttc gcg gcg gcg gct        1007
Val Glu Arg Gly Lys Leu Leu Ala Glu Asp Gly Phe Ala Ala Ala Ala
320                 325                 330                 335 gaa gca att ggc ggg gag atc gag ggg aaa ttg aaa aac aga gat gag        1055
Glu Ala Ile Gly Gly Glu Ile Glu Gly Lys Leu Lys Asn Arg Asp Glu
                340                 345                 350 att ttg aga gga gcg gag aat tgg atg tcg gac ata ttc aaa tgc ttc        1103
Ile Leu Arg Gly Ala Glu Asn Trp Met Ser Asp Ile Phe Lys Cys Phe
            355                 360                 365 ggg atg agc gtg ctc gga gtt tct gga tcg ccg aaa ttc gat ctg ttg        1151
Gly Met Ser Val Leu Gly Val Ser Gly Ser Pro Lys Phe Asp Leu Leu
        370                 375                 380 aag gca gat ttc gga tgg gga aag gcg agg aaa ttg gag gtg ctg tcg        1199
Lys Ala Asp Phe Gly Trp Gly Lys Ala Arg Lys Leu Glu Val Leu Ser
    385                 390                 395 att gat gga gag aat cac tca atg tcg ctg tgt agc tcg agc gat ttc        1247
Ile Asp Gly Glu Asn His Ser Met Ser Leu Cys Ser Ser Ser Asp Phe
400                 405                 410                 415 aat ggc gga ttg gag gtg ggt ttg tca ttg cct aga gag aga atg gcg        1295
Asn Gly Gly Leu Glu Val Gly Leu Ser Leu Pro Arg Glu Arg Met Ala
                420                 425                 430 gca ttt gca gag gtg ttt act gat gga ctt gcc aat ctt tgaataatta        1344
Ala Phe Ala Glu Val Phe Thr Asp Gly Leu Ala Asn Leu
            435                 440 tcattttata gttattaatt aaatatcttg catcccgtcc aatagtaata tcttaattat      1404
attcgatatt ccttcataaa aatattgaca tttgaaataa taacaatcaa attaattaaa      1464
taaaagc                                                                1471

<210> SEQ ID NO 4
<211> LENGTH: 444
<212> TYPE: PRT
<213> ORGANISM: Artificial Sequence
<220> FEATURE:
<223> OTHER INFORMATION: Description of Artificial Sequence:Amino acid
                        sequence of malonyltransferase SgMaT1' of
                        Salvia guaranitica

<400> SEQUENCE: 4

Thr Thr Leu Leu Glu Thr Cys His Ile Pro Pro Pro Pro Ala Asn
 1               5                  10                  15
```

-continued

```
Asp Leu Ser Ile Pro Leu Ser Phe Phe Asp Ile Lys Trp Leu His Tyr
            20                  25                  30
His Pro Val Arg Arg Leu Leu Phe Tyr His His Pro Ser Ser Lys Ser
        35                  40                  45
Gln Phe Leu His Thr Ile Val Pro His Leu Lys Gln Ser Leu Ser Leu
    50                  55                  60
Ala Leu Thr His Tyr Leu Pro Val Ala Gly Asn Leu Leu Tyr Pro Ser
65                  70                  75                  80
Asn Pro Glu Lys Phe Pro Gln Leu Arg Tyr Ala Ala Arg Asp Ser Val
                85                  90                  95
Pro Val Thr Ile Ala Glu Ser Asn Ser Asp Phe Glu Ser Leu Thr Gly
            100                 105                 110
Asn His Thr Arg Asp Ala Asp Gln Phe Tyr Asp Leu Leu Pro Pro Ile
        115                 120                 125
Pro Pro Ile Glu Glu Glu Ser Asp Trp Lys Leu Ile Asn Ile Phe Ala
    130                 135                 140
Val Gln Ile Thr Leu Phe Pro Gly Glu Gly Ile Cys Val Gly Phe Ser
145                 150                 155                 160
Asn His His Cys Leu Gly Asp Ala Arg Ser Met Val Gly Phe Ile Ser
                165                 170                 175
Ala Trp Gly Glu Ile Asn Gly Ile Gly Gly Tyr Glu Gly Phe Leu Ser
            180                 185                 190
Asn His Ser Asp Ser Leu Ser Leu Pro Ile Phe Asp Arg Ser Phe Ile
        195                 200                 205
Asn Asp Pro Asn Lys Ile Asp Ala Ile Phe Trp Lys Val Met Arg Asn
    210                 215                 220
Ile Pro Leu Lys Thr Ala Ser Phe Pro Leu Pro Thr Asn Arg Val Arg
225                 230                 235                 240
Ser Thr Phe Leu Leu Arg Arg Ser Asp Ile Glu Lys Leu Lys Thr Ala
                245                 250                 255
Thr Lys Ser Pro Ala Ser Ser Phe Val Ala Ala Ala Phe Val Trp
            260                 265                 270
Ser Cys Met Val Lys Ser Gly Asp Lys Ser Asp Glu Asn Ala Pro Glu
        275                 280                 285
Leu Phe Ile Ile Pro Ala Asp Ala Arg Gly Arg Ile Asp Pro Pro Ile
    290                 295                 300
Pro Glu Asn Tyr Phe Gly Asn Cys Ile Val Ser Ser Val Ala Arg Val
305                 310                 315                 320
Glu Arg Gly Lys Leu Leu Ala Glu Asp Gly Phe Ala Ala Ala Glu
                325                 330                 335
Ala Ile Gly Gly Glu Ile Glu Gly Lys Leu Lys Asn Arg Asp Glu Ile
            340                 345                 350
Leu Arg Gly Ala Glu Asn Trp Met Ser Asp Ile Phe Lys Cys Phe Gly
        355                 360                 365
Met Ser Val Leu Gly Val Ser Gly Ser Pro Lys Phe Asp Leu Leu Lys
    370                 375                 380
Ala Asp Phe Gly Trp Gly Lys Ala Arg Lys Leu Glu Val Leu Ser Ile
385                 390                 395                 400
Asp Gly Glu Asn His Ser Met Ser Leu Cys Ser Ser Asp Phe Asn
                405                 410                 415
Gly Gly Leu Glu Val Gly Leu Ser Leu Pro Arg Glu Arg Met Ala Ala
            420                 425                 430
```

```
                    Phe Ala Glu Val Phe Thr Asp Gly Leu Ala Asn Leu
                            435                 440

<210> SEQ ID NO 5
<211> LENGTH: 1530
<212> TYPE: DNA
<213> ORGANISM: Salvia guaranitica

<400> SEQUENCE: 5
aaaatccaca actttttccc ctccaacctc aaatttccac agccacc atg tcc acc           56
                                                   Met Ser Thr
                                                     1 acc gtg ctc gaa acc tcc gcc atc tcc cct ccg ccg ggc tcc gcc gcc         104
Thr Val Leu Glu Thr Ser Ala Ile Ser Pro Pro Pro Gly Ser Ala Ala
      5                  10                  15 gac ctc acc ctc ccc ctc tgc ttc ttc gac atc atc tgg ctc cat ttc         152
Asp Leu Thr Leu Pro Leu Cys Phe Phe Asp Ile Ile Trp Leu His Phe
 20                  25                  30                  35 cac ccc atc cgc cgc ctc atc ttc tac aac cac cct tgc acc gag gca         200
His Pro Ile Arg Arg Leu Ile Phe Tyr Asn His Pro Cys Thr Glu Ala
                 40                  45                  50 gaa ttc tcc tcc acc gtc gtc cca aac ctc aaa cac tcc ctc tct ctc         248
Glu Phe Ser Ser Thr Val Val Pro Asn Leu Lys His Ser Leu Ser Leu
             55                  60                  65 acc ctc caa cac ttc ccc ccc gtc gcc ggc aac ctc ctc ttc cct gtc         296
Thr Leu Gln His Phe Pro Pro Val Ala Gly Asn Leu Leu Phe Pro Val
         70                  75                  80 gac acc gat aaa tcc cgc ccc ttc ctc cgc tac gtc tcc ggc gac acc         344
Asp Thr Asp Lys Ser Arg Pro Phe Leu Arg Tyr Val Ser Gly Asp Thr
     85                  90                  95 gcc ccc ctc act atc gca gtt tcc ggg cgc gac ttc gac gaa tta gtc         392
Ala Pro Leu Thr Ile Ala Val Ser Gly Arg Asp Phe Asp Glu Leu Val
100                 105                 110                 115 gcc gga agc cac gcc cga gac tcc gac caa ttc tac gaa ttc ctc ccc         440
Ala Gly Ser His Ala Arg Asp Ser Asp Gln Phe Tyr Glu Phe Leu Pro
                120                 125                 130 ctg atg ccc ccg atc gcc gag gaa gaa aat tac aaa att gcc cct ctc         488
Leu Met Pro Pro Ile Ala Glu Glu Glu Asn Tyr Lys Ile Ala Pro Leu
            135                 140                 145 atc gcg ctc cag gct acg ctc ttc ccc ggc cgt ggg atc tgc atc ggg         536
Ile Ala Leu Gln Ala Thr Leu Phe Pro Gly Arg Gly Ile Cys Ile Gly
        150                 155                 160 gtg agc aat cac cac tgc ctc ggc gac gcc agg tcg atc gtc gga ttc         584
Val Ser Asn His His Cys Leu Gly Asp Ala Arg Ser Ile Val Gly Phe
165                 170                 175 gtc tgg gcc tgg gcc gag act aac aga aac aac ggg gac gag cgg ctg         632
Val Trp Ala Trp Ala Glu Thr Asn Arg Asn Asn Gly Asp Glu Arg Leu
180                 185                 190                 195 aga aac cgc tcg ccc ctt ctg att tat gac agg tcg tta gtt ttt ggg         680
Arg Asn Arg Ser Pro Leu Leu Ile Tyr Asp Arg Ser Leu Val Phe Gly
                200                 205                 210 gac acc caa aaa gct gac gaa aag tac tgg agc gtg atg aga aac atc         728
Asp Thr Gln Lys Ala Asp Glu Lys Tyr Trp Ser Val Met Arg Asn Ile
            215                 220                 225 cga cta acg tca tca agt ttt cct gtg cct cgt ggc agg gtc agg gcc         776
Arg Leu Thr Ser Ser Ser Phe Pro Val Pro Arg Gly Arg Val Arg Ala
        230                 235                 240 gcg ttc aca ctg cac cat tca gat att aaa aaa ctc aaa aat aag gtt         824
Ala Phe Thr Leu His His Ser Asp Ile Lys Lys Leu Lys Asn Lys Val
245                 250                 255
```

-continued

| | | |
|---|---|---|
| ttg tct aaa aat ccg gac cta gtt ttt gtc tcg tct ttt gca gtc acg<br>Leu Ser Lys Asn Pro Asp Leu Val Phe Val Ser Ser Phe Ala Val Thr<br>260                        265                      270                   275 | 872 |
| gcg gcg tac acg tgg agc tct gtg gtg aag tcc gcg cgc gcg gcc ggg<br>Ala Ala Tyr Thr Trp Ser Ser Val Val Lys Ser Ala Arg Ala Ala Gly<br>                    280                    285                   290 | 920 |
| gag gag gtg gat gac gat cga gac gag gtt ttc ttt ttt cct gcg gac<br>Glu Glu Val Asp Asp Asp Arg Asp Glu Val Phe Phe Phe Pro Ala Asp<br>295                        300                      305 | 968 |
| gcg agg ggc cgg ccg aac gct atg gtt gac cca ccc gtg ccg gtt aat<br>Ala Arg Gly Arg Pro Asn Ala Met Val Asp Pro Pro Val Pro Val Asn<br>          310                    315                    320 | 1016 |
| tac ttc ggg aac tgt tta ggc ggc ggg atg atc aag atg gag cat aag<br>Tyr Phe Gly Asn Cys Leu Gly Gly Gly Met Ile Lys Met Glu His Lys<br>325                        330                      335 | 1064 |
| aag gtg gcg gcg gag gaa gga ttc gtg gcg gcg gcg gag gcg att gct<br>Lys Val Ala Ala Glu Glu Gly Phe Val Ala Ala Ala Glu Ala Ile Ala<br>340                        345                    350                   355 | 1112 |
| gat caa atc aat aat gtg gtg aat aac aag gag aat ttt ttg aaa gga<br>Asp Gln Ile Asn Asn Val Val Asn Asn Lys Glu Asn Phe Leu Lys Gly<br>                    360                    365                   370 | 1160 |
| gcg gat aat tgg ttg tcg gag atg ccg aaa ttt ggg gaa ttg agc act<br>Ala Asp Asn Trp Leu Ser Glu Met Pro Lys Phe Gly Glu Leu Ser Thr<br>          375                    380                    385 | 1208 |
| ttt ggc gtt tcc ggt tcg ccg aaa ttc gat ttg ttg aat tcg gat ttc<br>Phe Gly Val Ser Gly Ser Pro Lys Phe Asp Leu Leu Asn Ser Asp Phe<br>                    390                    395                   400 | 1256 |
| ggg tgg ggg acg ggg tcg agg ttg gag gtt ctg tcg atg gat aag gag<br>Gly Trp Gly Thr Gly Ser Arg Leu Glu Val Leu Ser Met Asp Lys Glu<br>405                        410                      415 | 1304 |
| aag tat tcg atg tcg ttg tgt aat tcg tcg gat tct cct ggc ggt ttg<br>Lys Tyr Ser Met Ser Leu Cys Asn Ser Ser Asp Ser Pro Gly Gly Leu<br>420                        425                    430                   435 | 1352 |
| gtg gtg gga ttg tca ctt cct aag gag agg atg gac gct ttc gca act<br>Val Val Gly Leu Ser Leu Pro Lys Glu Arg Met Asp Ala Phe Ala Thr<br>                    440                    445                   450 | 1400 |
| atc ttt gac gat ggt ctt aaa ttt tgagtgtttg attttgttat ttaattttt<br>Ile Phe Asp Asp Gly Leu Lys Phe<br>455 | 1454 |
| tttaaagttt tgttgcttca aggtataaaa atttaagtca tttgatatga tagattttat<br>cacgtaagtt tttaac | 1514<br>1530 |

<210> SEQ ID NO 6
<211> LENGTH: 459
<212> TYPE: PRT
<213> ORGANISM: Artificial Sequence
<220> FEATURE:
<223> OTHER INFORMATION: Description of Artificial Sequence:Amino acid
        sequence of malonyltransferase SgMaT2 of Salvia
        guaranitica

<400> SEQUENCE: 6

Met Ser Thr Thr Val Leu Glu Thr Ser Ala Ile Ser Pro Pro Gly
1                  5                    10                   15

Ser Ala Ala Asp Leu Thr Leu Pro Leu Cys Phe Phe Asp Ile Ile Trp
                  20                    25                   30

Leu His Phe His Pro Ile Arg Arg Leu Ile Phe Tyr Asn His Pro Cys
              35                    40                   45

Thr Glu Ala Glu Phe Ser Ser Thr Val Val Pro Asn Leu Lys His Ser
50                        55                    60

Leu Ser Leu Thr Leu Gln His Phe Pro Pro Val Ala Gly Asn Leu Leu
 65                  70                  75                  80

Phe Pro Val Asp Thr Asp Lys Ser Arg Pro Phe Leu Arg Tyr Val Ser
                 85                  90                  95

Gly Asp Thr Ala Pro Leu Thr Ile Ala Val Ser Gly Arg Asp Phe Asp
            100                 105                 110

Glu Leu Val Ala Gly Ser His Ala Arg Asp Ser Asp Gln Phe Tyr Glu
        115                 120                 125

Phe Leu Pro Leu Met Pro Pro Ile Ala Glu Glu Asn Tyr Lys Ile
    130                 135                 140

Ala Pro Leu Ile Ala Leu Gln Ala Thr Leu Phe Pro Gly Arg Gly Ile
145                 150                 155                 160

Cys Ile Gly Val Ser Asn His His Cys Leu Gly Asp Ala Arg Ser Ile
                165                 170                 175

Val Gly Phe Val Trp Ala Trp Ala Glu Thr Asn Arg Asn Asn Gly Asp
            180                 185                 190

Glu Arg Leu Arg Asn Arg Ser Pro Leu Leu Ile Tyr Asp Arg Ser Leu
        195                 200                 205

Val Phe Gly Asp Thr Gln Lys Ala Asp Glu Lys Tyr Trp Ser Val Met
    210                 215                 220

Arg Asn Ile Arg Leu Thr Ser Ser Ser Phe Pro Val Pro Arg Gly Arg
225                 230                 235                 240

Val Arg Ala Ala Phe Thr Leu His His Ser Asp Ile Lys Lys Leu Lys
                245                 250                 255

Asn Lys Val Leu Ser Lys Asn Pro Asp Leu Val Phe Val Ser Ser Phe
            260                 265                 270

Ala Val Thr Ala Ala Tyr Thr Trp Ser Ser Val Lys Ser Ala Arg
        275                 280                 285

Ala Ala Gly Glu Glu Val Asp Asp Arg Asp Glu Val Phe Phe Phe
        290                 295                 300

Pro Ala Asp Ala Arg Gly Arg Pro Asn Ala Met Val Asp Pro Val
305                 310                 315                 320

Pro Val Asn Tyr Phe Gly Asn Cys Leu Gly Gly Met Ile Lys Met
                325                 330                 335

Glu His Lys Lys Val Ala Ala Glu Glu Gly Phe Val Ala Ala Glu
            340                 345                 350

Ala Ile Ala Asp Gln Ile Asn Asn Val Val Asn Asn Lys Glu Asn Phe
        355                 360                 365

Leu Lys Gly Ala Asp Asn Trp Leu Ser Glu Met Pro Lys Phe Gly Glu
    370                 375                 380

Leu Ser Thr Phe Gly Val Ser Gly Ser Pro Lys Phe Asp Leu Leu Asn
385                 390                 395                 400

Ser Asp Phe Gly Trp Gly Thr Gly Ser Arg Leu Glu Val Leu Ser Met
                405                 410                 415

Asp Lys Glu Lys Tyr Ser Met Ser Leu Cys Asn Ser Ser Asp Ser Pro
            420                 425                 430

Gly Gly Leu Val Val Gly Leu Ser Leu Pro Lys Glu Arg Met Asp Ala
        435                 440                 445

Phe Ala Thr Ile Phe Asp Asp Gly Leu Lys Phe
        450                 455

<210> SEQ ID NO 7
<211> LENGTH: 15
<212> TYPE: PRT

```
<213> ORGANISM: Artificial Sequence
<220> FEATURE:
<223> OTHER INFORMATION: Description of Artificial Sequence:Partial amino
      acid sequence of malonyltransferase

<400> SEQUENCE: 7

Tyr Ala Ala Gly Asp Ser Val Pro Val Thr Ile Ala Ala Ser Asn
 1               5                  10                  15

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence:Partial amino
      acid sequence of malonyltransferase

<400> SEQUENCE: 8

Leu Leu Phe Tyr His His Pro Ser Ser Lys
 1               5                  10

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence:Partial
      amino acid sequence of malonyltransferase

<400> SEQUENCE: 9

Ser Gly Asp Lys Ser Asp Glu Asn Ala Pro Glu Leu Phe Ile Ile Pro
 1               5                  10                  15

Ala Asp Ala

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence:Partial
      amino acid sequence of malonyltransferase

<400> SEQUENCE: 10

Met Ala Ala Phe Glu Glu Val Phe
 1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:Partial
      amino acid sequence of malonyltransferase

<400> SEQUENCE: 11

Trp Leu His Tyr His Pro Val
 1               5

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence:Partial
      amino acid sequence of malonyltransferase

<400> SEQUENCE: 12
```

```
Gly Ala Glu Asn Trp Met Ser Asp Ile Phe Lys
 1               5                  10
```

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence:Partial
      amino acid sequence of malonyltransferase
<220> FEATURE:
<221> NAME/KEY: Unsure
<222> LOCATION: (5)
<223> OTHER INFORMATION: Xaa can be any amino acid

<400> SEQUENCE: 13

```
Leu Ala Ala Glu Xaa Gly Phe Ala Val Ala Ala Ala Ile Gly Gly
 1               5                  10                  15

Gly Ile Ile Gly
            20
```

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence:Partial
      amino acid sequence of malonyltransferase

<400> SEQUENCE: 14

```
Ser Phe Ile Asn Asp Pro Asn Lys Ile Asp Ala Ile Phe
 1               5                  10
```

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence:Partial
      amino acid sequence of malonyltransferase

<400> SEQUENCE: 15

```
Thr Ala Ser Phe Pro Leu Pro Thr Asn Arg
 1               5                  10
```

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence:Partial
      amino acid sequence of malonyltransferase

<400> SEQUENCE: 16

```
Phe Pro Gln Leu Arg
 1               5
```

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:Partial
      amino acid sequence of malonyltransferase

<400> SEQUENCE: 17

```
Ala Asp Phe Gly Trp Gly Lys
 1               5
```

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence:Partial
      amino acid sequence of malonyltransferase

<400> SEQUENCE: 18

Asp Ala Asp Gln Phe Tyr Asp Leu Leu Pro Pro Ile Pro Pro
 1               5                  10

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (6)
<223> OTHER INFORMATION: n=inosine
<220> FEATURE:
<221> NAME/KEY: misc_feature
<222> LOCATION: (9)
<223> OTHER INFORMATION: n=inosine
<220> FEATURE:
<221> NAME/KEY: misc_feature
<222> LOCATION: (12)
<223> OTHER INFORMATION: n=inosine
<220> FEATURE:
<221> NAME/KEY: misc_feature
<222> LOCATION: (18)
<223> OTHER INFORMATION: n=inosine
<220> FEATURE:
<221> NAME/KEY: misc_feature
<222> LOCATION: (21)
<223> OTHER INFORMATION: n=inosine
<220> FEATURE:
<221> NAME/KEY: misc_feature
<222> LOCATION: (24)
<223> OTHER INFORMATION: n=inosine

<400> SEQUENCE: 19
taygcngcng gngaytcngt nccngt                                          26

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (3)
<223> OTHER INFORMATION: n=inosine
<220> FEATURE:
<221> NAME/KEY: misc_feature
<222> LOCATION: (6)
<223> OTHER INFORMATION: n=inosine
<220> FEATURE:
<221> NAME/KEY: misc_feature
<222> LOCATION: (9)
<223> OTHER INFORMATION: n=inosine
<220> FEATURE:
<221> NAME/KEY: misc_feature
<222> LOCATION: (12)
<223> OTHER INFORMATION: n=inosine
<220> FEATURE:
<221> NAME/KEY: misc_feature
<222> LOCATION: (18)
<223> OTHER INFORMATION: n=inosine -continued

```
<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:Primer
<220> FEATURE:
<221> NAME/KEY: misc_feature
<222> LOCATION: (4)
<223> OTHER INFORMATION: n=inosine
<220> FEATURE:
<221> NAME/KEY: misc_feature
<222> LOCATION: (10)
<223> OTHER INFORMATION: n=inosine
<220> FEATURE:
<221> NAME/KEY: misc_feature
<222> LOCATION: (19)
<223> OTHER INFORMATION: n=inosine

<400> SEQUENCE: 21
yttnccccan ccraartcng c                                              21

<210> SEQ ID NO 22
<211> LENGTH: 1636
<212> TYPE: DNA
<213> ORGANISM: Salvia splendens

<400> SEQUENCE: 22
```

```
ca aca aca aca aca atc ctc gaa aca tgc cac att cca ccg ccg ccg        47
   Thr Thr Thr Thr Ile Leu Glu Thr Cys His Ile Pro Pro Pro Pro
    1               5                  10                  15 gcg gcc aac gac ctc tca atc ccc ctc tcc ttc ttc gac atc aaa tgg       95
Ala Ala Asn Asp Leu Ser Ile Pro Leu Ser Phe Phe Asp Ile Lys Trp
                 20                  25                  30 ctc cac tac cac ccc gtc cgc cgc ctc ctc ttc tac cac cac cct tcc      143
Leu His Tyr His Pro Val Arg Arg Leu Leu Phe Tyr His His Pro Ser
             35                  40                  45 tcc aaa tcc caa ttc ctc cac aca atc gtt cca cac ctc aaa caa tca      191
Ser Lys Ser Gln Phe Leu His Thr Ile Val Pro His Leu Lys Gln Ser
         50                  55                  60 ctc tct ctc gct ctc aca cac tac ctc ccc gtc gcc ggc aac ctc ctc      239
Leu Ser Leu Ala Leu Thr His Tyr Leu Pro Val Ala Gly Asn Leu Leu
 65                  70                  75 tac ccg tcc aac acc gaa aaa ttc ccc caa ctc cgc tac gcc gcc ggg      287
Tyr Pro Ser Asn Thr Glu Lys Phe Pro Gln Leu Arg Tyr Ala Ala Gly
 80                  85                  90                  95 gat tcc gtc ccg gtg acg atc gcg gag tcc aat tcc gac ttc gaa agc      335
Asp Ser Val Pro Val Thr Ile Ala Glu Ser Asn Ser Asp Phe Glu Ser
                100                 105                 110 ctt acc gga aac cac acg cgc gac gcc gat caa ttc tac gat ctc ctc      383
Leu Thr Gly Asn His Thr Arg Asp Ala Asp Gln Phe Tyr Asp Leu Leu
            115                 120                 125 ccg cct att cct ccg att gag gag gaa tcg gat tgg aaa ttg atc aac      431
Pro Pro Ile Pro Pro Ile Glu Glu Glu Ser Asp Trp Lys Leu Ile Asn
        130                 135                 140 att ttc gcg gtt cag atc act ctg ttc ccc ggc gaa gga atc tgc atc      479
Ile Phe Ala Val Gln Ile Thr Leu Phe Pro Gly Glu Gly Ile Cys Ile
145                 150                 155 ggt ttc tcc aat cac cac tgc ctc ggc gac gcc aga tct atc gtc gga      527
Gly Phe Ser Asn His His Cys Leu Gly Asp Ala Arg Ser Ile Val Gly
160                 165                 170                 175
```

-continued

| | |
|---|---|
| ttc atc tcc gct tgg ggt gaa atc aac gga atc gga gga tat gaa gga<br>Phe Ile Ser Ala Trp Gly Glu Ile Asn Gly Ile Gly Gly Tyr Glu Gly<br>180 185 190 | 575 |
| ttc tta tcc aat cac agt gat tct ctc tcc ctt ccg att ttc gat cga<br>Phe Leu Ser Asn His Ser Asp Ser Leu Ser Leu Pro Ile Phe Asp Arg<br>195 200 205 | 623 |
| tcg ttt att aac gat ccg aac aaa atc gac gct att ttc tgg aaa gtg<br>Ser Phe Ile Asn Asp Pro Asn Lys Ile Asp Ala Ile Phe Trp Lys Val<br>210 215 220 | 671 |
| ctg aga aac ata cca ttg aaa acg gcg tcg ttt ccg ctg cct acg aac<br>Leu Ser Asn Met Pro Leu Lys Thr Ala Ser Phe Pro Leu Pro Thr Asn<br>225 230 235 | 719 |
| aga gtc aga tct aca ttc ctc ctc cgc aga tcc gac atc gag aag ctg<br>Ser Val Ser Ser Thr Phe Leu Leu Arg Ser Ser Asp Ile Glu Lys Leu<br>240 245 250 255 | 767 |
| aaa acc gcc act aaa tcg ccg gcg tcg tcg ttc gtc gcg gca gca gcg<br>Lys Thr Ala Thr Lys Ser Pro Ala Ser Ser Phe Val Ala Ala Ala Ala<br>260 265 270 | 815 |
| ttc gtc tgg agc tgt atg gtg aaa tcc ggc gac aaa tcc gac gaa aat<br>Phe Val Trp Ser Cys Met Val Lys Ser Gly Asp Lys Ser Asp Glu Asn<br>275 280 285 | 863 |
| gcg cct gag ctt ttc atc ata cct gcg gac gcc agg ggg agg gtg gat<br>Ala Pro Glu Leu Phe Ile Met Pro Ala Asp Ala Ser Gly Ser Val Asp<br>290 295 300 | 911 |
| ccg ccg ata ccg gag aat tac ttc ggc aac tgc atc gtg agc tcg gtg<br>Pro Pro Met Pro Glu Asn Tyr Phe Gly Asn Cys Ile Val Ser Ser Val<br>305 310 315 | 959 |
| gcg cag gtg gag cgc ggg aag ctg gcg gcg gag gat gga ttc gcg gtg<br>Ala Gln Val Glu Arg Gly Lys Leu Ala Ala Glu Asp Gly Phe Ala Val<br>320 325 330 335 | 1007 |
| gcg gct gaa gca att ggc ggg gag atc gag ggg aaa ttg aaa aac aga<br>Ala Ala Glu Ala Ile Gly Gly Glu Ile Glu Gly Lys Leu Lys Asn Ser<br>340 345 350 | 1055 |
| gat gag att ttg aga gga gcg gag aat tgg atg tcg gac ata ttc aaa<br>Asp Glu Ile Leu Ser Gly Ala Glu Asn Trp Met Ser Asp Ile Phe Lys<br>355 360 365 | 1103 |
| tgc ttc ggg atg agc gtg ctc gga gtt tct gga tcg ccg aaa ttc gat<br>Cys Phe Gly Met Ser Val Leu Gly Val Ser Gly Ser Pro Lys Phe Asp<br>370 375 380 | 1151 |
| ctg ttg aag gcg gat ttt gga tgg gga aag gcg agg aaa ttg gag gtg<br>Leu Leu Lys Ala Asp Phe Gly Trp Gly Lys Ala Arg Lys Leu Glu Val<br>385 390 395 | 1199 |
| ctg tcg att gat gga gag aat cac tca atg tcg ctg tgt agc tcg agc<br>Leu Ser Ile Asp Gly Glu Asn His Ser Met Ser Leu Cys Ser Ser Ser<br>400 405 410 415 | 1247 |
| gat ttc aat ggc gga ttg gag gtg ggt ttg tcg ttg ccc aga gag aga<br>Asp Phe Asn Gly Gly Leu Glu Val Gly Leu Ser Leu Pro Arg Glu Arg<br>420 425 430 | 1295 |
| atg gcg gca ttt gaa gag gtg ttt aga gca tcc ata atg gcg gcg agc<br>Met Ala Ala Phe Glu Glu Val Phe Arg Ala Ser Ile Met Ala Ala Ser<br>435 440 445 | 1343 |
| gga ccg gct agg cga tct ccg gcg ctc gtc gaa cca ttg taaccggcga<br>Gly Pro Ala Arg Arg Ser Pro Ala Leu Val Glu Pro Leu<br>450 455 460 | 1392 |
| gcgccatttc ggcgaaaaaa tcggcgagcg caggccgatt cgcgagagcg ctgggcgatg | 1452 |
| cgctcgccgc cattgcaggc tccggaccgg ggagcgatcg gcgagcaaaa ttttcttttt | 1512 |
| cttttaattt tcgaaactct atatgtacgc gttttgcacg tcattttcat tcgcatcact | 1572 |

-continued

```
tgttttaacg agtactctct ctatcttaat ttctatataa gatcaacaac gtgaaatgaa   1632
gaac                                                                1636
```

<210> SEQ ID NO 23
<211> LENGTH: 460
<212> TYPE: PRT
<213> ORGANISM: Salvia splendens

<400> SEQUENCE: 23

```
Thr Thr Thr Thr Ile Leu Glu Thr Cys His Ile Pro Pro Pro Pro Ala
  1               5                  10                  15

Ala Asn Asp Leu Ser Ile Pro Leu Ser Phe Phe Asp Ile Lys Trp Leu
             20                  25                  30

His Tyr His Pro Val Arg Arg Leu Leu Phe Tyr His His Pro Ser Ser
         35                  40                  45

Lys Ser Gln Phe Leu His Thr Ile Val Pro His Leu Lys Gln Ser Leu
     50                  55                  60

Ser Leu Ala Leu Thr His Tyr Leu Pro Val Ala Gly Asn Leu Leu Tyr
 65                  70                  75                  80

Pro Ser Asn Thr Glu Lys Phe Pro Gln Leu Arg Tyr Ala Ala Gly Asp
                 85                  90                  95

Ser Val Pro Val Thr Ile Ala Glu Ser Asn Ser Asp Phe Glu Ser Leu
            100                 105                 110

Thr Gly Asn His Thr Arg Asp Ala Asp Gln Phe Tyr Asp Leu Leu Pro
        115                 120                 125

Pro Ile Pro Pro Ile Glu Glu Ser Asp Trp Lys Leu Ile Asn Ile
    130                 135                 140

Phe Ala Val Gln Ile Thr Leu Phe Pro Gly Glu Gly Ile Cys Ile Gly
145                 150                 155                 160

Phe Ser Asn His His Cys Leu Gly Asp Ala Ser Ser Ile Val Gly Phe
                165                 170                 175

Ile Ser Ala Trp Gly Glu Ile Asn Gly Ile Gly Gly Tyr Glu Gly Phe
            180                 185                 190

Leu Ser Asn His Ser Asp Ser Leu Ser Leu Pro Ile Phe Asp Arg Ser
        195                 200                 205

Phe Ile Asn Asp Pro Asn Lys Ile Asp Ala Ile Phe Trp Lys Val Leu
    210                 215                 220

Ser Asn Met Pro Leu Lys Thr Ala Ser Phe Pro Leu Pro Thr Asn Ser
225                 230                 235                 240

Val Ser Ser Thr Phe Leu Leu Arg Ser Ser Asp Ile Glu Lys Leu Lys
                245                 250                 255

Thr Ala Thr Lys Ser Pro Ala Ser Ser Phe Val Ala Ala Ala Phe
            260                 265                 270

Val Trp Ser Cys Met Val Lys Ser Gly Asp Lys Ser Asp Glu Asn Ala
        275                 280                 285

Pro Glu Leu Phe Ile Met Pro Ala Asp Ala Ser Gly Ser Val Asp Pro
    290                 295                 300

Pro Met Pro Glu Asn Tyr Phe Gly Asn Cys Ile Val Ser Ser Val Ala
305                 310                 315                 320

Gln Val Glu Arg Gly Lys Leu Ala Ala Glu Asp Gly Phe Ala Val Ala
                325                 330                 335

Ala Glu Ala Ile Gly Gly Glu Ile Glu Gly Lys Leu Lys Asn Ser Asp
            340                 345                 350

Glu Ile Leu Ser Gly Ala Glu Asn Trp Met Ser Asp Met Phe Lys Cys
```

-continued

```
                     355                 360                 365
Phe Gly Met Ser Val Leu Gly Val Ser Gly Ser Pro Lys Phe Asp Leu
    370                 375                 380

Leu Lys Ala Asp Phe Gly Trp Gly Lys Ala Ser Lys Leu Glu Val Leu
385                 390                 395                 400

Ser Ile Asp Gly Glu Asn His Ser Met Ser Leu Cys Ser Ser Ser Asp
                405                 410                 415

Phe Asn Gly Gly Leu Glu Val Gly Leu Ser Leu Pro Ser Glu Ser Met
            420                 425                 430

Ala Ala Phe Glu Glu Val Phe Ser Ala Ser Met Met Ala Ala Ser Gly
            435                 440                 445

Pro Ala Ser Arg Ser Pro Ala Leu Val Glu Pro Leu
    450                 455                 460

<210> SEQ ID NO 24
<211> LENGTH: 1498
<212> TYPE: DNA
<213> ORGANISM: Salvia splendens

<400> SEQUENCE: 24 gcaactttt  cccctccaac ctataatttc cacaaccacc atg acc acc acc              52
                                            Met Thr Thr Thr
                                              1 gtg ctc gaa acc tcc gcc atc tcc cct ccg ccg ggc tcc gcc gcc gac        100
Val Leu Glu Thr Ser Ala Ile Ser Pro Pro Pro Gly Ser Ala Ala Asp
  5              10                  15                  20 ctc acc ctc ccc ctc tgc ttc ttc gac atc atc tgg ctc cat ttc cac        148
Leu Thr Leu Pro Leu Cys Phe Phe Asp Ile Ile Trp Leu His Phe His
             25                  30                  35 ccc atc cgc cgc ctc atc ttc tac aac cac cct tgc acc gag gcc gaa        196
Pro Ile Arg Arg Leu Ile Phe Tyr Asn His Pro Cys Thr Glu Ala Glu
         40                  45                  50 ttc tcc tcc acc atc gtc cca aac ctc aaa cac tcc ctc tct ctc acc        244
Phe Ser Ser Thr Ile Val Pro Asn Leu Lys His Ser Leu Ser Leu Thr
     55                  60                  65 ctc caa cac ttc ccc ccc gtc gcc ggc aac ctc ctc ttc cct gtc gac        292
Leu Gln His Phe Pro Pro Val Ala Gly Asn Leu Leu Phe Pro Val Asp
 70                  75                  80 acc gat aaa tcc cgc ccc ttc ctc cgc tac gtc tcc ggc gac acc gcc        340
Thr Asp Lys Ser Arg Pro Phe Leu Arg Tyr Val Ser Gly Asp Thr Ala
 85                  90                  95                 100 ccc ctc acg atc gcc gtc tcc ggg cgc gac ttc gac gaa tta gtc gct        388
Pro Leu Thr Ile Ala Val Ser Gly Arg Asp Phe Asp Glu Leu Val Ala
                105                 110                 115 ggc agc cgc gcc cga gac tcc gac caa ttc tac gaa ttc ctc ccc ctg        436
Gly Ser Arg Ala Arg Asp Ser Asp Gln Phe Tyr Glu Phe Leu Pro Leu
            120                 125                 130 atg ccc ccg atc gcc gag gag gaa gat tac aaa att gcc cct ctc atc        484
Met Pro Pro Ile Ala Glu Glu Glu Asp Tyr Lys Ile Ala Pro Leu Ile
        135                 140                 145 gcg ctc cag gcc acg ctc ttc ccc ggc cgc ggg atc tgc atc ggg gtg        532
Ala Leu Gln Ala Thr Leu Phe Pro Gly Arg Gly Ile Cys Ile Gly Val
    150                 155                 160 agc aat cac cac tgc ctc ggt gac gcc agg tcg atc gtt gca ttc gtc        580
Ser Asn His His Cys Leu Gly Asp Ala Arg Ser Ile Val Ala Phe Val
165                 170                 175                 180 tcg gcc tgg gcc gag acg aac aga aac agc ggg gac gag cgg ctg aga        628
Ser Ala Trp Ala Glu Thr Asn Arg Asn Ser Gly Asp Glu Arg Leu Arg
                185                 190                 195
```

```
aac tgc acg ctc ccg ctg att tat gat agg tcg tca gtt ttt ggg gac      676
Asn Cys Thr Leu Pro Leu Ile Tyr Asp Arg Ser Ser Val Phe Gly Asp
        200                 205                 210 acc caa aaa gct gac gaa aag tac tgg agc gtg atg aga aac atc ccg      724
Thr Gln Lys Ala Asp Glu Lys Tyr Trp Ser Val Met Arg Asn Ile Pro
    215                 220                 225 ctg aca tca tca agt ttt cct gtg cct agt ggc agg gtc agg gcc gcg      772
Leu Thr Ser Ser Ser Phe Pro Val Pro Ser Gly Arg Val Arg Ala Ala
        230                 235                 240 ttc aca ctg cac cag tca gat att aaa aac ctc aaa aat aag gtt ttg      820
Phe Thr Leu His Gln Ser Asp Ile Lys Asn Leu Lys Asn Lys Val Leu
245                 250                 255                 260 tct aaa aat ccg gac cta gtt ttc gtc tcg tct ttt gcc gtc acg gcg      868
Ser Lys Asn Pro Asp Leu Val Phe Val Ser Ser Phe Ala Val Thr Ala
            265                 270                 275 gcg tac acg tgg agc tct gtg gtg aag tcc gcg cgc gcg gcc ggg gag      916
Ala Tyr Thr Trp Ser Ser Val Val Lys Ser Ala Arg Ala Ala Gly Glu
                280                 285                 290 gag gtg gat gac gat cgt gac gag gtt ttc ttt ttt cct gcg gac gcg      964
Glu Val Asp Asp Asp Arg Asp Glu Val Phe Phe Phe Pro Ala Asp Ala
            295                 300                 305 agg ggt cgg ccg aac gct atg gtt gac ccg ccc gtg ccg gtt aat tac     1012
Arg Gly Arg Pro Asn Ala Met Val Asp Pro Pro Val Pro Val Asn Tyr
    310                 315                 320 ttc ggg aac tgt tta ggc ggc ggg atg atc aag atg gag cat aag aag     1060
Phe Gly Asn Cys Leu Gly Gly Gly Met Ile Lys Met Glu His Lys Lys
325                 330                 335                 340 gtg gcg gcg gag gaa gga ttc gtg gcg gcg gcg gag gcg att gct gat     1108
Val Ala Ala Glu Glu Gly Phe Val Ala Ala Ala Glu Ala Ile Ala Asp
            345                 350                 355 caa atc aat aat gtg gtg aat aac aag gat aat ttt ttg aaa gga gcg     1156
Gln Ile Asn Asn Val Val Asn Asn Lys Asp Asn Phe Leu Lys Gly Ala
                360                 365                 370 gat aat tgg ttg tcg gag atg ccg aaa ttt ggg gaa ttg agc act ttt     1204
Asp Asn Trp Leu Ser Glu Met Pro Lys Phe Gly Glu Leu Ser Thr Phe
            375                 380                 385 ggc gtt tcc ggt tcg ccg aaa ttc gat ttg ttg aat tcg gat ttc ggg     1252
Gly Val Ser Gly Ser Pro Lys Phe Asp Leu Leu Asn Ser Asp Phe Gly
    390                 395                 400 tgg ggg acg ggg tcg agg ttg gag gtt ctg tcg atg gat aag gag aag     1300
Trp Gly Thr Gly Ser Arg Leu Glu Val Leu Ser Met Asp Lys Glu Lys
405                 410                 415                 420 tat tcg atg tcg ttg tgt aat tcg tcg gat tct cct ggc ggt ttg gtg     1348
Tyr Ser Met Ser Leu Cys Asn Ser Ser Asp Ser Pro Gly Gly Leu Val
            425                 430                 435 gtc gga ttg tca ctt cct aag gag agg atg gat gct ttc gca act atc     1396
Val Gly Leu Ser Leu Pro Lys Glu Arg Met Asp Ala Phe Ala Thr Ile
                440                 445                 450 ttt gaa gat ggt ctt aaa ttt tgagtgtttg attttgttat ttaatttttt        1447
Phe Glu Asp Gly Leu Lys Phe
455 tttaaagttt tgttgcttca agggttaaaa atttaagtca tttgatatga t            1498

<210> SEQ ID NO 25
<211> LENGTH: 459
<212> TYPE: PRT
<213> ORGANISM: Salvia splendens

<400> SEQUENCE: 25
```

-continued

```
Met Thr Thr Thr Val Leu Glu Thr Ser Ala Ile Ser Pro Pro Gly
 1               5                  10                 15

Ser Ala Ala Asp Leu Thr Leu Pro Leu Cys Phe Phe Asp Ile Ile Trp
             20                  25                 30

Leu His Phe His Pro Ile Arg Arg Leu Ile Phe Tyr Asn His Pro Cys
         35                  40                 45

Thr Glu Ala Glu Phe Ser Ser Thr Ile Val Pro Asn Leu Lys His Ser
     50                  55                 60

Leu Ser Leu Thr Leu Gln His Phe Pro Val Ala Gly Asn Leu Leu
 65                 70                  75                 80

Phe Pro Val Asp Thr Asp Lys Ser Arg Pro Phe Leu Arg Tyr Val Ser
                 85                  90                 95

Gly Asp Thr Ala Pro Leu Thr Ile Ala Val Ser Gly Arg Asp Phe Asp
             100                 105                110

Glu Leu Val Ala Gly Ser Arg Ala Arg Asp Ser Asp Gln Phe Tyr Glu
         115                 120                 125

Phe Leu Pro Leu Met Pro Pro Ile Ala Glu Glu Asp Tyr Lys Ile
     130                 135                 140

Ala Pro Leu Ile Ala Leu Gln Ala Thr Leu Phe Pro Gly Arg Gly Ile
145                 150                 155                 160

Cys Ile Gly Val Ser Asn His His Cys Leu Gly Asp Ala Arg Ser Ile
                 165                 170                 175

Val Ala Phe Val Ser Ala Trp Ala Glu Thr Asn Arg Asn Ser Gly Asp
             180                 185                 190

Glu Arg Leu Arg Asn Cys Thr Leu Pro Leu Ile Tyr Asp Arg Ser Ser
         195                 200                 205

Val Phe Gly Asp Thr Gln Lys Ala Asp Glu Lys Tyr Trp Ser Val Met
     210                 215                 220

Arg Asn Ile Pro Leu Thr Ser Ser Phe Pro Val Pro Ser Gly Arg
225                 230                 235                 240

Val Arg Ala Ala Phe Thr Leu His Gln Ser Asp Ile Lys Asn Leu Lys
                 245                 250                 255

Asn Lys Val Leu Ser Lys Asn Pro Asp Leu Val Phe Val Ser Ser Phe
             260                 265                 270

Ala Val Thr Ala Ala Tyr Thr Trp Ser Ser Val Lys Ser Ala Arg
         275                 280                 285

Ala Ala Gly Glu Glu Val Asp Asp Arg Asp Glu Val Phe Phe Phe
     290                 295                 300

Pro Ala Asp Ala Arg Gly Arg Pro Asn Ala Met Val Asp Pro Val
305                 310                 315                 320

Pro Val Asn Tyr Phe Gly Asn Cys Leu Gly Gly Met Ile Lys Met
                 325                 330                 335

Glu His Lys Lys Val Ala Ala Glu Gly Phe Val Ala Ala Glu
             340                 345                 350

Ala Ile Ala Asp Gln Ile Asn Asn Val Val Asn Asn Lys Asp Asn Phe
         355                 360                 365

Leu Lys Gly Ala Asp Asn Trp Leu Ser Glu Met Pro Lys Phe Gly Glu
     370                 375                 380

Leu Ser Thr Phe Gly Val Ser Gly Ser Pro Lys Phe Asp Leu Leu Asn
385                 390                 395                 400

Ser Asp Phe Gly Trp Gly Thr Gly Ser Arg Leu Glu Val Leu Ser Met
                 405                 410                 415

Asp Lys Glu Lys Tyr Ser Met Ser Leu Cys Asn Ser Ser Asp Ser Pro
```

```
                     420                 425                 430
         Gly Gly Leu Val Val Gly Leu Ser Leu Pro Lys Glu Arg Met Asp Ala
                 435                 440                 445

Phe Ala Thr Ile Phe Glu Asp Gly Leu Lys Phe
                 450                 455

<210> SEQ ID NO 26
<211> LENGTH: 1502
<212> TYPE: DNA
<213> ORGANISM: Perilla frutescens

<400> SEQUENCE: 26
aattaacata tatttatatt tagtcc atg aca aca aca ttg ctc gaa              47
                             Met Thr Thr Thr Leu Leu Glu
                              1               5 acc tgc cgg att ctg cca ccg ccg acc gac gag gtc tcg atc cct ctc      95
Thr Cys Arg Ile Leu Pro Pro Pro Thr Asp Glu Val Ser Ile Pro Leu
             10                  15                  20 tct ttc ttc gac atg aag tgg ctc cac ttc cac ccc ctc cgc cgt ctc     143
Ser Phe Phe Asp Met Lys Trp Leu His Phe His Pro Leu Arg Arg Leu
         25                  30                  35 ctc ttc tac gac cac cct tgt tcc aag ccc caa ttc ttg gat gcc att     191
Leu Phe Tyr Asp His Pro Cys Ser Lys Pro Gln Phe Leu Asp Ala Ile
     40                  45                  50                  55 gtt cca cac ctc aaa caa tct ctc tcc ctc act ctc aaa cac tac ctc     239
Val Pro His Leu Lys Gln Ser Leu Ser Leu Thr Leu Lys His Tyr Leu
                 60                  65                  70 ccc gtc gcc ggc aat ctg ctc tac cct tca tca aac acc gac caa aag     287
Pro Val Ala Gly Asn Leu Leu Tyr Pro Ser Ser Asn Thr Asp Gln Lys
             75                  80                  85 ccc cga ctt cgc tgc gtc gcc ggg gat tca gtc ccg ctg acg atc gcg     335
Pro Arg Leu Arg Cys Val Ala Gly Asp Ser Val Pro Leu Thr Ile Ala
         90                  95                 100 gag tcc acc acc gat ttc gac atg ctc acc gga aat cat gca aga gat     383
Glu Ser Thr Thr Asp Phe Asp Met Leu Thr Gly Asn His Ala Arg Asp
    105                 110                 115 gcc gat cag ttc tac gat ttc gtg gcg ccg atg cca cct att gca gag     431
Ala Asp Gln Phe Tyr Asp Phe Val Ala Pro Met Pro Pro Ile Ala Glu
120                 125                 130                 135 gaa ttc gaa tgc aaa ata gtt ccc gtt ttc tcc ctg caa gtg acg ctg     479
Glu Phe Glu Cys Lys Ile Val Pro Val Phe Ser Leu Gln Val Thr Leu
                140                 145                 150 ttt cct ggg cgt gga att tgc atc ggt tta tcc aat cat cac tgc ctc     527
Phe Pro Gly Arg Gly Ile Cys Ile Gly Leu Ser Asn His His Cys Leu
            155                 160                 165 ggc gac gcc aga tcg gtg gtg gga ttc gtg ttg gcg tgg gct tcc atc     575
Gly Asp Ala Arg Ser Val Val Gly Phe Val Leu Ala Trp Ala Ser Ile
        170                 175                 180 aat aaa ttc ggt ggt gat gag gag ttt ctg tcg gaa aac ggt gaa tct     623
Asn Lys Phe Gly Gly Asp Glu Glu Phe Leu Ser Glu Asn Gly Glu Ser
    185                 190                 195 ttg ccg att ttt gat cga tct ttg att aag gat cca ctc gaa atc gat     671
Leu Pro Ile Phe Asp Arg Ser Leu Ile Lys Asp Pro Leu Glu Ile Asp
200                 205                 210                 215 act att ttc tgg aaa gta ttg aga aac ata cct ctg aag ccg tca tct     719
Thr Ile Phe Trp Lys Val Leu Arg Asn Ile Pro Leu Lys Pro Ser Ser
                220                 225                 230 ttt ccg tta ccc acc aac aga gtc aga gcc aca ttc gtt ctc agt caa     767
Phe Pro Leu Pro Thr Asn Arg Val Arg Ala Thr Phe Val Leu Ser Gln
            235                 240                 245
```

-continued

```
tcc gac ata aaa agg cta aaa cat ttg gcg aat aac aac cta gtt caa      815
Ser Asp Ile Lys Arg Leu Lys His Leu Ala Asn Asn Asn Leu Val Gln
        250                 255                 260 ccg tcg tct ttc gtc gtc gcg gct gcg tat att tgg agc tgc atg gtg      863
Pro Ser Ser Phe Val Val Ala Ala Ala Tyr Ile Trp Ser Cys Met Val
265                 270                 275 aaa tcc ggc gac gga ggt gag gct aac gcg ccg gaa ttg ttc gtt att      911
Lys Ser Gly Asp Gly Gly Glu Ala Asn Ala Pro Glu Leu Phe Val Ile
280                 285                 290                 295 cca gcc gac gcg aga ggc cgg acg aat ccg ccg gtg ccg gcg aat tac      959
Pro Ala Asp Ala Arg Gly Arg Thr Asn Pro Pro Val Pro Ala Asn Tyr
                300                 305                 310 ttc ggg aat tgc ata gtt ggc ggg gta gta aaa gtg gag cac gaa aag     1007
Phe Gly Asn Cys Ile Val Gly Gly Val Val Lys Val Glu His Glu Lys
            315                 320                 325 atg gcg gga aac gag gga ttt gtg att gct gca gaa gcc ata gct ggg     1055
Met Ala Gly Asn Glu Gly Phe Val Ile Ala Ala Glu Ala Ile Ala Gly
        330                 335                 340 gaa atc aag aac aag atg aat gat aaa gag gag att ttg aaa ggg gcg     1103
Glu Ile Lys Asn Lys Met Asn Asp Lys Glu Glu Ile Leu Lys Gly Ala
345                 350                 355 gag aat tgg ctg tcg gaa atc tgg aaa tgt atg ggg atg agc gtg ctc     1151
Glu Asn Trp Leu Ser Glu Ile Trp Lys Cys Met Gly Met Ser Val Leu
360                 365                 370                 375 gga att tct ggt tcg ccg aaa ttc gat tta tcg aat gca gat ttt gga     1199
Gly Ile Ser Gly Ser Pro Lys Phe Asp Leu Ser Asn Ala Asp Phe Gly
                380                 385                 390 tgg gga aag gcg agg aaa ctg gaa gtt gtg tcg atc gat gga gag aag     1247
Trp Gly Lys Ala Arg Lys Leu Glu Val Val Ser Ile Asp Gly Glu Lys
            395                 400                 405 tat acg atg tcg ttg tgt aat tcc gac tgt ggg ttg gag gtt ggg ttg     1295
Tyr Thr Met Ser Leu Cys Asn Ser Asp Cys Gly Leu Glu Val Gly Leu
        410                 415                 420 tcg ttg ccg gga gaa aga atg gaa gct ttt gca gcc ata ttt gcc gat     1343
Ser Leu Pro Gly Glu Arg Met Glu Ala Phe Ala Ala Ile Phe Ala Asp
425                 430                 435 ggc cta gct aag cta gat agc tca tgattcatga ataatatata tatatatata   1397
Gly Leu Ala Lys Leu Asp Ser Ser
440                 445 tatagagaga gagagagaat tgatatgccc atctttgtgg gcgccgctga tcgtcatcac   1457
tttatttatt cttttttttt ttggtaattt tcgcttttct cccag                  1502

<210> SEQ ID NO 27
<211> LENGTH: 447
<212> TYPE: PRT
<213> ORGANISM: Perilla frutescens

<400> SEQUENCE: 27

Met Thr Thr Thr Leu Leu Glu Thr Cys Arg Ile Leu Pro Pro Pro Thr
 1               5                  10                  15

Asp Glu Val Ser Ile Pro Leu Ser Phe Phe Asp Met Lys Trp Leu His
             20                  25                  30

Phe His Pro Leu Arg Arg Leu Leu Phe Tyr Asp His Pro Cys Ser Lys
         35                  40                  45

Pro Gln Phe Leu Asp Ala Ile Val Pro His Leu Lys Gln Ser Leu Ser
     50                  55                  60

Leu Thr Leu Lys His Tyr Leu Pro Val Ala Gly Asn Leu Leu Tyr Pro
 65                  70                  75                  80
```

```
Ser Ser Asn Thr Asp Gln Lys Pro Arg Leu Arg Cys Val Ala Gly Asp
                85                  90                  95

Ser Val Pro Leu Thr Ile Ala Glu Ser Thr Thr Asp Phe Asp Met Leu
            100                 105                 110

Thr Gly Asn His Ala Arg Asp Ala Asp Gln Phe Tyr Asp Phe Val Ala
            115                 120                 125

Pro Met Pro Pro Ile Ala Glu Glu Phe Glu Cys Lys Ile Val Pro Val
130                 135                 140

Phe Ser Leu Gln Val Thr Leu Phe Pro Gly Arg Gly Ile Cys Ile Gly
145                 150                 155                 160

Leu Ser Asn His His Cys Leu Gly Asp Ala Arg Ser Val Val Gly Phe
                165                 170                 175

Val Leu Ala Trp Ala Ser Ile Asn Lys Phe Gly Gly Asp Glu Glu Phe
            180                 185                 190

Leu Ser Glu Asn Gly Glu Ser Leu Pro Ile Phe Asp Arg Ser Leu Ile
            195                 200                 205

Lys Asp Pro Leu Glu Ile Asp Thr Ile Phe Trp Lys Val Leu Arg Asn
210                 215                 220

Ile Pro Leu Lys Pro Ser Ser Phe Pro Leu Pro Thr Asn Arg Val Arg
225                 230                 235                 240

Ala Thr Phe Val Leu Ser Gln Ser Asp Ile Lys Arg Leu Lys His Leu
                245                 250                 255

Ala Asn Asn Asn Leu Val Gln Pro Ser Ser Phe Val Val Ala Ala Ala
                260                 265                 270

Tyr Ile Trp Ser Cys Met Val Lys Ser Gly Asp Gly Glu Ala Asn
                275                 280                 285

Ala Pro Glu Leu Phe Val Ile Pro Ala Asp Ala Arg Gly Arg Thr Asn
            290                 295                 300

Pro Pro Val Pro Ala Asn Tyr Phe Gly Asn Cys Ile Val Gly Val
305                 310                 315                 320

Val Lys Val Glu His Glu Lys Met Ala Gly Asn Glu Gly Phe Val Ile
                325                 330                 335

Ala Ala Glu Ala Ile Ala Gly Glu Ile Lys Asn Lys Met Asn Asp Lys
                340                 345                 350

Glu Glu Ile Leu Lys Gly Ala Glu Asn Trp Leu Ser Glu Ile Trp Lys
                355                 360                 365

Cys Met Gly Met Ser Val Leu Gly Ile Ser Gly Ser Pro Lys Phe Asp
            370                 375                 380

Leu Ser Asn Ala Asp Phe Gly Trp Gly Lys Ala Arg Lys Leu Glu Val
385                 390                 395                 400

Val Ser Ile Asp Gly Glu Lys Tyr Thr Met Ser Leu Cys Asn Ser Asp
                405                 410                 415

Cys Gly Leu Glu Val Gly Leu Ser Leu Pro Gly Glu Arg Met Glu Ala
                420                 425                 430

Phe Ala Ala Ile Phe Ala Asp Gly Leu Ala Lys Leu Asp Ser Ser
                435                 440                 445

<210> SEQ ID NO 28
<211> LENGTH: 1502
<212> TYPE: DNA
<213> ORGANISM: Lavendula angustifolia

<400> SEQUENCE: 28 ggc acg aga att aga acc gcc atg act acc acc gtg att gaa acc acg     48
```

```
                                                                -continued

Gly Thr Arg Ile Arg Thr Ala Met Thr Thr Thr Val Ile Glu Thr Thr
 1               5                  10                  15 gga gtc cca cct ccg ccg ggc gcc gcc gcg gag cta acg gtg cca ctc      96
Gly Val Pro Pro Pro Pro Gly Ala Ala Ala Glu Leu Thr Val Pro Leu
             20                  25                  30 tgt ttc atg gac ttc gtt tgg ctt cat ttc cac ccc atc cgc cgc ctt     144
Cys Phe Met Asp Phe Val Trp Leu His Phe His Pro Ile Arg Arg Leu
         35                  40                  45 att ttc tac gac cac cct tgc tct gaa tcc gac ttc cta aac gac gtc     192
Ile Phe Tyr Asp His Pro Cys Ser Glu Ser Asp Phe Leu Asn Asp Val
     50                  55                  60 gtt ccg aag ctc aaa cac tca ctc tct ctc gct cta cag aac tat ctc     240
Val Pro Lys Leu Lys His Ser Leu Ser Leu Ala Leu Gln Asn Tyr Leu
 65                  70                  75                  80 ccg gta gct gca aac tta ctc tac cct tca gat tta aac aca gac gag     288
Pro Val Ala Ala Asn Leu Leu Tyr Pro Ser Asp Leu Asn Thr Asp Glu
                 85                  90                  95 aag ccc cta atc cgt tac gtc tcc ggc gat ggg gtt ccg ctc acc gtc     336
Lys Pro Leu Ile Arg Tyr Val Ser Gly Asp Gly Val Pro Leu Thr Val
            100                 105                 110 gcc gtc tca gcc gcc gac ttc gac gag ctc acc gga ttt cac gtg aag     384
Ala Val Ser Ala Ala Asp Phe Asp Glu Leu Thr Gly Phe His Val Lys
        115                 120                 125 gaa tca gat caa ttt tac gat ttc atg ccg gag atg ccg ccg gtg agg     432
Glu Ser Asp Gln Phe Tyr Asp Phe Met Pro Glu Met Pro Pro Val Arg
    130                 135                 140 gag gaa gct ggg tgc aat tac aaa att atc cct ctc atc gcc gtg cag     480
Glu Glu Ala Gly Cys Asn Tyr Lys Ile Ile Pro Leu Ile Ala Val Gln
145                 150                 155                 160 gtg act ctc ttc ccc ggc cgc ggg att tgc gtc ggt tta tcc aac cac     528
Val Thr Leu Phe Pro Gly Arg Gly Ile Cys Val Gly Leu Ser Asn His
                165                 170                 175 cac tgc ctc ggc gac gcc aga tcc gtc gtc ggg ttc atg tgg cgg tgg     576
His Cys Leu Gly Asp Ala Arg Ser Val Val Gly Phe Met Trp Arg Trp
            180                 185                 190 gcg gag atc aac aaa tcc ggc ggg gac gag gat tct caa tcg caa aac     624
Ala Glu Ile Asn Lys Ser Gly Gly Asp Glu Asp Ser Gln Ser Gln Asn
        195                 200                 205 ggc gag tcg ttg ccg ctt ttc gat cga tcg gtt ttc gga gat cgt gat     672
Gly Glu Ser Leu Pro Leu Phe Asp Arg Ser Val Phe Gly Asp Arg Asp
    210                 215                 220 aaa gtt aac aat atg ttt tgg gac gcg atg aag agg aaa ccg ttc gaa     720
Lys Val Asn Asn Met Phe Trp Asp Ala Met Lys Arg Lys Pro Phe Glu
225                 230                 235                 240 gcg gcg tcg ttt ccg tta ccg acg aac aga gtg aga gga gcg ttc agc     768
Ala Ala Ser Phe Pro Leu Pro Thr Asn Arg Val Arg Gly Ala Phe Ser
                245                 250                 255 ctc gac cca tcc gcc att aaa aag ctt aag aac cga gtt ttg tcc agt     816
Leu Asp Pro Ser Ala Ile Lys Lys Leu Lys Asn Arg Val Leu Ser Ser
            260                 265                 270 aac caa acc cta tcc cac gtc tcc tcc ttc gtc gtg acg gct gcg tac     864
Asn Gln Thr Leu Ser His Val Ser Ser Phe Val Val Thr Ala Ala Tyr
        275                 280                 285 gtc tgg acc tcc gtg gtg aaa tcc gcc gac gcc gcc gga gag gaa gtc     912
Val Trp Thr Ser Val Val Lys Ser Ala Asp Ala Ala Gly Glu Glu Val
    290                 295                 300 gcc gga gac gaa gcc gat att ttc ttc ttt ccg gcc gac ggc agg ggc     960
Ala Gly Asp Glu Ala Asp Ile Phe Phe Phe Pro Ala Asp Gly Arg Gly
305                 310                 315                 320
```

```
cgg ccg aac gcc atg gtt gac caa ccg gtg cca ctt aac tac ttc gga    1008
Arg Pro Asn Ala Met Val Asp Gln Pro Val Pro Leu Asn Tyr Phe Gly
                325                 330                 335 aac ttt ttg ggc ggc ggg atg gtc aag atg gag cat aaa aag gtg gcg    1056
Asn Phe Leu Gly Gly Gly Met Val Lys Met Glu His Lys Lys Val Ala
            340                 345                 350 gcg gag gac ggg ttt ctc gcg gtg gcg gag gcc atc tcc gat caa att    1104
Ala Glu Asp Gly Phe Leu Ala Val Ala Glu Ala Ile Ser Asp Gln Ile
        355                 360                 365 aag aac aat atc aac aat aaa gaa gtt ttc atg aaa ggt acg gaa aat    1152
Lys Asn Asn Ile Asn Asn Lys Glu Val Phe Met Lys Gly Thr Glu Asn
    370                 375                 380 tgg ttg tcg gaa atg gcg aaa gtt cct atg atg aga tca ttt gga gtt    1200
Trp Leu Ser Glu Met Ala Lys Val Pro Met Met Arg Ser Phe Gly Val
385                 390                 395                 400 tct ggt tcg ccc aaa ttc gat ttg tcg aaa gcc gat ttc gga tgg ggg    1248
Ser Gly Ser Pro Lys Phe Asp Leu Ser Lys Ala Asp Phe Gly Trp Gly
                405                 410                 415 aag gcg aga agg ctt gaa gtt ttg tcg atg gac gga gag aag tat tca    1296
Lys Ala Arg Arg Leu Glu Val Leu Ser Met Asp Gly Glu Lys Tyr Ser
            420                 425                 430 atg tcg ttg tgt aat tca tca agt agc gac ggt gga tta gtc gtc gga    1344
Met Ser Leu Cys Asn Ser Ser Ser Asp Gly Gly Leu Val Val Gly
        435                 440                 445 gtt tcg ttg ccg gcg gta aga atg gag gct ttt gct tct ata ttt gaa    1392
Val Ser Leu Pro Ala Val Arg Met Glu Ala Phe Ala Ser Ile Phe Glu
    450                 455                 460 gat ggg tta aaa tct taaattccgt tatttcgtta cttgcacaag ttcaaactat    1447
Asp Gly Leu Lys Ser
465             469 ttcatgaata aaattacttc gatttgaaca aaaaaaaaaa aaaaaaaaaa aaaaa       1502
```

<210> SEQ ID NO 29
<211> LENGTH: 469
<212> TYPE: PRT
<213> ORGANISM: Lavendula angustifolia

<400> SEQUENCE: 29

```
Gly Thr Arg Ile Arg Thr Ala Met Thr Thr Thr Val Ile Glu Thr Thr
1               5                   10                  15

Gly Val Pro Pro Pro Gly Ala Ala Ala Glu Leu Thr Val Pro Leu
                20                  25                  30

Cys Phe Met Asp Phe Val Trp Leu His Phe His Pro Ile Arg Arg Leu
            35                  40                  45

Ile Phe Tyr Asp His Pro Cys Ser Glu Ser Asp Phe Leu Asn Asp Val
        50                  55                  60

Val Pro Lys Leu Lys His Ser Leu Ser Leu Ala Leu Gln Asn Tyr Leu
65                  70                  75                  80

Pro Val Ala Ala Asn Leu Leu Tyr Pro Ser Asp Leu Asn Thr Asp Glu
                85                  90                  95

Lys Pro Leu Ile Arg Tyr Val Ser Gly Asp Gly Val Pro Leu Thr Val
            100                 105                 110

Ala Val Ser Ala Ala Asp Phe Asp Glu Leu Thr Gly Phe His Val Lys
        115                 120                 125

Glu Ser Asp Gln Phe Tyr Asp Phe Met Pro Glu Met Pro Pro Val Arg
    130                 135                 140

Glu Glu Ala Gly Cys Asn Tyr Lys Ile Ile Pro Leu Ile Ala Val Gln
145                 150                 155                 160
```

```
Val Thr Leu Phe Pro Gly Arg Gly Ile Cys Val Gly Leu Ser Asn His
            165                 170                 175

His Cys Leu Gly Asp Ala Arg Ser Val Val Gly Phe Met Trp Arg Trp
        180                 185                 190

Ala Glu Ile Asn Lys Ser Gly Gly Asp Glu Asp Ser Gln Ser Gln Asn
            195                 200                 205

Gly Glu Ser Leu Pro Leu Phe Asp Arg Ser Val Phe Gly Asp Arg Asp
        210                 215                 220

Lys Val Asn Asn Met Phe Trp Asp Ala Met Lys Arg Lys Pro Phe Glu
225                 230                 235                 240

Ala Ala Ser Phe Pro Leu Pro Thr Asn Arg Val Arg Gly Ala Phe Ser
                245                 250                 255

Leu Asp Pro Ser Ala Ile Lys Lys Leu Lys Asn Arg Val Leu Ser Ser
            260                 265                 270

Asn Gln Thr Leu Ser His Val Ser Ser Phe Val Thr Ala Ala Tyr
        275                 280                 285

Val Trp Thr Ser Val Val Lys Ser Ala Asp Ala Gly Glu Glu Val
    290                 295                 300

Ala Gly Asp Glu Ala Asp Ile Phe Phe Phe Pro Ala Asp Gly Arg Gly
305                 310                 315                 320

Arg Pro Asn Ala Met Val Asp Gln Pro Val Pro Leu Asn Tyr Phe Gly
                325                 330                 335

Asn Phe Leu Gly Gly Gly Met Val Lys Met Glu His Lys Lys Val Ala
            340                 345                 350

Ala Glu Asp Gly Phe Leu Ala Val Ala Glu Ala Ile Ser Asp Gln Ile
        355                 360                 365

Lys Asn Asn Ile Asn Asn Lys Glu Val Phe Met Lys Gly Thr Glu Asn
    370                 375                 380

Trp Leu Ser Glu Met Ala Lys Val Pro Met Met Arg Ser Phe Gly Val
385                 390                 395                 400

Ser Gly Ser Pro Lys Phe Asp Leu Ser Lys Ala Asp Phe Gly Trp Gly
                405                 410                 415

Lys Ala Arg Arg Leu Glu Val Leu Ser Met Asp Gly Glu Lys Tyr Ser
            420                 425                 430

Met Ser Leu Cys Asn Ser Ser Ser Asp Gly Gly Leu Val Val Gly
        435                 440                 445

Val Ser Leu Pro Ala Val Arg Met Glu Ala Phe Ala Ser Ile Phe Glu
    450                 455                 460

Asp Gly Leu Lys Ser
465             469

<210> SEQ ID NO 30
<211> LENGTH: 35
<212> TYPE: DNA
<213> ORGANISM: Artificial sequence
<220> FEATURE:
<223> OTHER INFORMATION: Description of Artificial Sequence:Primer No.1

<400> SEQUENCE: 30
ggatccatcg agggacgcat gacaacaaca acaac                              35

<210> SEQ ID NO 31
<211> LENGTH: 33
<212> TYPE: DNA
<213> ORGANISM: Artificial sequence
<220> FEATURE:
```

-continued

```
<223> OTHER INFORMATION: Description of Artificial Sequence:Primer No.2

<400> SEQUENCE: 31
ggatccttac aatggttcga cgagcgccgg aga                                33

<210> SEQ ID NO 32
<211> LENGTH: 28
<212> TYPE: DNA
<213> ORGANISM: Artificial sequence
<220> FEATURE:
<223> OTHER INFORMATION: Description of Artificial Sequence:Primer No.3

<400> SEQUENCE: 32
ggacccgccg ataccggaaa attacttc                                      28
```

US 7,186,886 B2

ALIPHATIC ACYL TRANSFERASE GENES

FIELD OF THE INVENTION

The present invention relates to a gene encoding a protein which has an activity to transfer an aliphatic acyl group to a glycosyl group at the 5-position of flavonoids, and to a method of using same.

RELATED ART

In the floriculture industry, it is important to develop new and different varieties of flowering plants. In particular, flower colour is one of the most important characteristics of flowering plants, and classical breeding techniques that rely on crossing have been used extensively to develop new varieties exhibiting various colours. However, since genetic resources are very limited for a particular plant species in which crossing can be carried out, it is rare for a single plant species to have a full spectrum of colour varieties.

Flower colour is predominantly due to a class of compounds, generally called anthocyanins, which belong to flavonoids. It has been known that there are various anthocyanins in plants, and the molecular structure of many of these compounds have already been determined. The colour of an anthocyanin is determined mainly by its structure (Harborne (1986) The Flavonoids, p. 565). Research has been conducted on enzymes, and genes encoding these enzymes, involved in biosynthesis of anthocyanins. There are instances, for example, in which techniques in molecular biology were applied, and genes were introduced into plants to alter flower colours (Holton et al. (1995) Plant Cell, 7, p. 1071; Tanaka et al. (1998) Plant Cell Physiol. 39. p. 1119). The biochemical pathway for biosynthesis of anthocyanins up to anthocyanidin 3-glucosides is common in most flowering plats (Holton et al. (1995) Plant Cell, 7, p. 1071). Thereafter, anthocyanidin 3-glucosides present in plants are subjected to diverse modifications specific to species or varieties. The diversity of this modification is one of the causes for the diversity of flower colours.

Although anthocyanins are unstable compounds in neutral solution, their stability is improved by modification with a glycosyl or an acyl group (Forkmann (1991) Plant Breeding, 106, p. 1). The colour of anthocynins becomes a little reddish by glycosylation, and becomes blue when an aromatic acyl group is added (Forkmann (1991) Plant Breeding, 106, p 1). The acyl groups are broadly divided into the aromatic acyl groups (for example, the caffeoyl group, the coumaroyl group, etc.) and the aliphatic acyl groups (for example, the malonyl group, the acetyl group, etc.). The physiological role of the aliphatic acyl group as concerns flower colour is not known, except that it increases the solubility of anthocyanins.

Several studies have been reported on purification and biochemical properties of enzymes having an activity to transfer an aliphatic acyl group to anthocyanins [Archives of Biochemistry and Biophysics, 1981, 208, 233–241 (Crude purification, molecular weight, and examination of substrate-specificity of Flavonol 3MaT (an enzyme catalyzing the reaction of transferring a malonyl group to a glycosyl group at the 3-position of a flavonol) and Flavone/Flavonol 7 MaT (an enzyme catalyzing the reaction of transferring a malonyl group to a glycosyl group at the 7-position of flavone and flavonol) of parsley); Archives of Biochemistry and Biophysics, 1983, 224, 261–271 (Measurement of activity of flavonol 3MaT and Flavone/Flavonol 7 MaT in various organs of parsley); Archives of Biochemistry and Biophysics, 1983, 226, 206–217 (Purification into single sample of Flavonol 3MaT and Flavone/Flavonol 7 MaT of parsley, and Preparation of 3MaT antibody); Eur. J. Biochem. 1983, 133, 439–448 (Confirmation of existence and structure of malonylated apigenin 7-0-glucoside in parsley by means of NMR etc.); Archives of Biochemistry and Biophysics, 1984, 234, 513–521 (Determination of optimum pH, molecular weight and Km of 7MaT for an isoflavone of a pea); Phytochemistry, 1993, 32, 1425–1426 (Confirmation of existence of aliphatic acyl transferase activity to cyanidin 3-glucoside in the crude extract from flower petals of Dendranthema morifolium, a plant belonging to Asteraceae); Plant Science, 1996, 118, 109–118 (Confirmation of malonyl transferase activity in crude extract from cultured cells of Ajuca reptans); Phytochemistry, 1999, 52, 15–18 (Determination of substrate specificity of malonyl transferase derived from flower petals of dahlia)]. However, the primary structures of the proteins has not been determined, nor has cloning of the gene been reported.

DISCLOSURE OF THE INVENTION

It is an object of the present invention to determine an effect of malonylation among acylation, by an aliphatic acyl transferase for transferring an acyl groups to anthocyanins upon colour of flowers, and to provide a gene which encodes a protein having an activity to transfer an aliphatic acyl group, preferably a gene which encodes a protein having an activity to transfer an aliphatic acyl group to anthocynins. It is possible to alter the colour of flowers by introducing a gene which encodes a protein having an activity to transfer an aliphatic acyl group, in accordance with the present invention, into a plant and by expressing the same.

As described above, there have been no reports on the effect of malonylation of anthocyanins upon flower colour. In order to determine this effect, the colour of three solutions of anthocyanins, that is, delphinidin 3,5-diglucoside, awobanin(delphinidin 3-(coumaroyl) glucoside-5-glucoside), malonyl-awobanin(delphinidin 3-(coumaroyl) glucoside-5-(malonyl)glucoside), was compared, and it was found that the colour of malonyl-awobanin is the bluest, indicating that malonylation causes anthocyanins to become bluer.

Thus, purification of a malonyl transferase was attempted using flowers of *salvia* as the material. Then, a partial amino acid sequences of the purified protein were determined, and based on this information, a DNA fragment of the gene encoding the malonyl transferase of *salvia* was amplified using the PCR method. Using this DNA fragment as a probe, the cDNA library of flower of *Salvia guaranitica* was screened, and two genes encoding malonyl transferase were obtained. Further, using these genes as probes, homologs were obtained from *Salvia splendens, perilla*, and lavender.

Therefore, according to the present invention, there is provided a gene encoding a protein which has an amino acid sequence according to any one of SEQ ID NO: 2, 4, 6, 23, 25, 27 or 29, and has an activity to transfer an aliphatic acyl group to a glycosyl group at the 5-position of flavonoids, or a gene encoding a protein which has any of these sequences modified by addition or deletion of one or more amino acids and/or substitution by other amino acids, and has activity for transferring an aliphatic acyl group to a glycosyl group at 5-position of flavonoids.

According to the present invention, there is also provided a gene encoding a protein which has an amino acid sequence exhibiting homology of 50% or more with any of the sequences according to SEQ ID NO: 2, 4, 6, 23, 25, 27 or 29, and has an activity to transfer an aliphatic acyl group to a glycosyl group at the 5-position of a flavonoids.

Further, according to the present invention, there is provided a gene which hybridizes to a part or all of the nucleotide sequences encoding any of the amino acid sequences according to SEQ ID NO: 2, 4, 6, 23, 25, 27 or 29 under the condition of 5×SSC, 50° C., and which encodes a protein having an activity to transfer an aliphatic acyl group to a glycosyl group at 5-position of flavonoids.

The present invention additionally provides a vector comprising the above-described gene.

The present invention also provides a host transformed by the above-described vector.

The present invention further provides a protein encoded by any of the above-described genes.

The present invention also provides a method of making the protein, comprising the steps of: culturing, or growing, the above-described host; and collecting, from the host, the protein having an activity to transfer an aliphatic acyl group to a glycosyl group at 5-position of flavonoids.

The present invention further provides a transgenic plant having the above-described gene introduced, or offspring of the plant or tissue thereof having the same property.

The present invention further provides a cut flower of the above-described plant or offspring thereof having the same property.

The present invention further provides a method of altering flower colour using the above-described gene.

The present invention further provides a method of making a flower blue by using the above-described gene.

PREFERRED EMBODIMENTS OF THE INVENTION

Genes of the present invention include, for example, those encoding amino acid sequences according to SEQ ID NO: 2, 4, 6, 23, 25, 27 and 29. However, it is known that a protein having an amino acid sequence that is modified by addition or deletion of plural amino acids and/or by substitution of other amino acids, exhibits the same enzyme activity as the original protein. Therefore, a protein having an amino acid sequence according to any one of SEQ ID NO: 2, 4, 6, 23, 25, 27 or 29 modified by addition or deletion of one or more amino acids and/or by substitution by other amino acids, and a gene encoding the protein, is within the scope of the present invention, as long as the protein has an activity to transfer an aliphatic acyl group to a glycosyl group at the 5-position of flavonoids.

The present invention also relates to a gene which hybridizes with a nucleotide sequence encoding amino acid sequences according to any one of SEQ ID NO: 2, 4, 6, 23, 25, 27 or 29, or a part of the nucleotide sequences, preferably a nucleotide sequence encoding 6 or more amino acids, for example, 6 or more amino acids in a concensus region, under the condition of, for example, 5×SSC, at 50° C., and which encodes a protein having an activity to transfer an aliphatic acyl group to a glycosyl group at the 5-position of flavonoids. A suitable hybridization temperature varies with the nucleotide sequence or the length thereof, and a temperature of 50° C. or lower is preferred when the probe is a DNA fragment of 18 bases encoding 6 amino acids.

Genes selected by such hybridization include naturally-occurring genes, including, but not limited to, genes derived from plants such as genes derived from petunia, torenia, etc. Also, a gene selected by hybridization may be either cDNA, or genome DNA.

Further, the present invention also relates to the use for altering flower colour, of a gene encoding a protein which has an amino acid sequence having a homology of about 50% or more, preferably 60% or 70% or more, further preferably 80% or 90% or more, with the amino acid sequence according to any one of SEQ ID NO: 2, 4, 6, 23, 25, 27 or 29, and which has an activity to transfer an aliphatic acyl group to a glycosyl group at the 5-position of flavonoids.

A gene having a native nucleotide sequence can be obtained, for example, by screening of a cDNA library, as shown more specifically in Examples. A DNA encoding a protein having a modified amino acid sequence can be synthesized starting from DNA having a native nucleotide sequence by means of usual methods such as a site-specific mutagenesis or the PCR method. For example, a DNA fragment to which a desired modification is to be introduced is first obtained by treatment of a native cDNA or genome DNA with restriction enzymes. Then, using this as a template, site-specific mutagenesis or the PCR method is performed with a primer having the desired mutation introduced therein, to obtain a DNA fragment having the desired modification introduced therein. Thereafter, the DNA fragment having the desired modification introduced therein may be ligated to a DNA fragment encoding other portions of the target protein.

Alternatively, in order to obtain DNA encoding a protein which has a shortened amino acid sequence, DNA encoding an amino acid sequence longer than the target amino acid sequence, such as the DNA encoding the full-length amino acid sequence, may be cut with suitable restriction enzymes. If the resulting DNA fragment does not encode the entire target amino acid sequence, a DNA fragment consisting of the missing sequence may be synthesized and ligated.

By expressing the obtained gene using a gene expression system in *Escherichia coli* and yeast, and by measuring the enzyme activity, it is possible to confirm that an obtained gene encodes a protein having an activity to transfer an aliphatic acyl group. It is also possible by expressing the gene to obtain, as a gene product, a protein having an activity to transfer an aliphatic acyl group. It is also possible by using an antibody to an amino acid sequence according to SEQ ID NO: 2, 4, 6, 23, 25, 27 or 29, to obtain a protein having an activity to transfer an aliphatic acyl group. Further, it is possible to use an antibody to clone a gene encoding a protein having an activity to transfer an aliphatic acyl group derived from other living organisms.

Therefore, the present invention relates to a recombination vector, especially an expression vector, comprising above described gene, and to a host transformed by the vector. Both procaryote and eukaryote may be used as a host. In procaryote, bacteria such as *Escherichia coli* that belongs to the genus *Escherichia*, or *Bacillus subtilis* that belongs to the genus *Bacillus* may be used as a usual host. As a eukaryotic host, a lower eukaryote, for example, a eukaryotic micro-organism such as yeast and fungi which belong to the fungi may be used.

In yeast, a micro-organism belonging to the genus *Saccharomyces* such as *Saccharomyces cerevisiae* or the like may be used as a host. In mold fungi, a micro-organism belonging to the genus *Aspergillus* such as *Aspergillus oryzae, Aspergillus niger*, and a micro-organism belonging to the genus *Penicillium*, may be used as hosts. Animal cells and plant cells may also be used as hosts. In animal cells, cell systems derived from a mouse, hamster, monkey, a human, etc. may be used. Insect cells such as silkworm cells, or even an adult silkworm itself, may be used as a host.

The expression vector of the present invention includes expression control regions depending upon the kind of host to which it is to be introduced, such as a promotor and a terminator, replication origin, and the like. As a promotor for an expression vector in bacteria, commonly used promotors such as a trc promotor, tac promotor, lac promotor or the like may be used. As a promotor for an expression vector in yeast, glyceraldehyde-3-phosphate dehydrogenase promotor, pH 05 promotor or the like, and as a promotor for an expression vector in fungi, an amylase promotor, a trpC promotor or the like may be used. As a promotor for an expression vector in animal cell hosts, a viral promotor such as SV 40 early promotor, SV 40 late promotor, or the like may be used. Construction of the expression vector may be performed in accordance with any of the usual methods known to those skilled in the art using restriction enzymes, ligases, etc. Transformation of host cells with the expression vector may also be performed in accordance with any of the usual methods.

The target protein can be obtained by culturing, raising or growing the host transformed with the above described expression vector, and by recovering a gene product from the culture or the like, and purifying in accordance with usual methods, for example filtration, centrifuging, disruption of cells, gel filtration chromatography, ion exchange chromatography, and the like.

The present invention is not limited to a gene derived from *salvia* and encoding a protein which has an activity to transfer an aliphatic acyl group. The present invention relates to use of a gene encoding a protein which has activity for transferring an aliphatic acyl group. The origin of the protein having an activity to transfer an aliphatic acyl group may be plants, animals, or microorganisms. Irrespective of the origin, such a protein can be equally applied to alteration of flower colour, as long as it has activity for transferring an aliphatic acyl group. Further, the present invention relates to a transgenic plant or its offspring or tissue thereof, including cut flowers, which is obtained by introducing a gene encoding a protein having activity to transfer an aliphatic acyl group, and which has its hue thereby modified.

By using the gene obtained according to the present invention, which encodes a protein having an activity to transfer an aliphatic acyl group, anthocyanins accumulated in vacuoles can be acylated so as to become blue, and as a result, flower colour can be altered to blue. In the present state of the art, it is possible to introduce a gene into a plant and to cause the gene to be expressed in a constitutive or tissue-specific fashion. It is also possible to suppress the expression of a target gene using, for example, an anti-sense method or a co-suppression method.

Examples of plants that can be transformed in this manner include, but are not limited to, roses, chrysanthemums, carnations, snapdragons, cyclamens, orchids, lisianthus, freesias, gerberas, gladiolus, gypsophila, kalanchoes, lilies, pelargoniums, geraniums, petunias, torenias, tulips, rice, barley, wheat, rapeseed, potatos, tomatos, poplars, bananas, eucalyptuses, sweet potatos, soybeans, alfalfa, lupine, and corn.

EXAMPLES

The present invention will be described in detail below in accordance with Examples thereof. Unless otherwise specified, the molecular biological techniques employed are those set forth in Molecular Cloning (Sambrook et al., 1989).

Example 1

Change of Colour of Various Anthocyanins Depending Upon pH

Delphinidin 3,5-diglucoside, awobanin (delphinidin 3-(coumaroyl) glucoside-5-glucoside), malonyl-awobanin (delphinidin 3-(coumaroyl)glucoside-5-(malonyl) glucoside) were dissolved in McIlvaine buffer (pH 5.3, pH 5.6, pH 6.0) in concentrations of 0.1 mM, 0.3 mM, 0.5 mM, respectively, and colours of the solutions were evaluated using Colour charts (Royal Horticulture Society). Delphinidin 3,5-diglucoside can be obtained from its 3,5-diacetylglucoside form by removing the acetyl portion in alkaline hydrolysis reaction (Tetrahedron, 48, 4313–4326, 1992).

Awobanin can be obtained from malonyl-awobanin by removing its 5-malonyl portion (Tetrahedron Lett. 24, 4863–4866, 1983). Malonyl-awobanin was obtained by extraction from plants using the method as set forth in Tetrahedron Lett. 24, 4863–4866, 1983. The greater the number in the Colour chart, the bluer the colour is. When the number is the same, symbol A represents the bluest colour. The results of the test are summarized in Table 1. In all concentrations and pH, malonyl-awobanin was the bluest, indicating that the malonyl group caused anthocyanins to become blue.

TABLE 1

| Anthocyanins | Concentration | Number in Colour chart at pH 5.3 | Number in Colour chart at pH 5.6 | Number in Colour chart at pH 6.0 |
|---|---|---|---|---|
| Delphinidin 3,5-diglucoside | 0.1 mM | 84C | 84C | too faint to be measured |
| Delphinidin 3,5-diglucoside | 0.3 mM | 85A | 86D | 88C |
| Delphinidin 3,5-diglucoside | 0.5 mM | 86D | 90B | 88B/C |
| Awobanin | 0.1 mM | 85C | 85A | 91B |
| Awobanin | 0.3 mM | 86D | not tested | 91A |
| Malonyl-awobanin | 0.1 mM | 85C | 91B | 91B |
| Malonyl-awobanin | 0.3 mM | 92A | 93B | 96C |
| Malonyl-awobanin | 0.5 mM | 93B | not tested | 96A |

Example 2

Measurement of Activity of Malonyl Transferase of *Salvia*

Measurement of activity of malonyl transferase was conducted using reaction solution 100 μl (potassium phosphate of final concentration of 20 mM, pH 7.0, containing shisonin 10 μg, malonyl CoA 10 μg, and an enzyme sample to be measured, dissolved in 0.01% trifluoro acetic acid). After reaction was carried out at 30° C. for 20 minutes, the reaction was terminated by adding 200 μl of 0.05% TFA aqueous solution cooled on ice. Quantification of shisonin and malonyl-shisonin was conducted by reverse phase high performance liquid chromatography (DYNAMAX HPLC system) using a Shodex Asahipak ODP-50 4E column, and using a linear concentration gradient with 0.5% TFA solution as the solution and 0.5% TFA, 50% acetonitrile aqueous solution as the solution, such that concentration of the B solution was 45%, 45%, 55%, 100%, 100%, 45%, and 45%, at time 0, 3, 17, 18, 23, 24, and 30 minutes, respectively, after the start of separation, at a flow rate of 0.7 ml/min, using 50 µl of reaction solution, monitoring absorption at 520 nm.

Example 3

Protein Purification of Malonyl Transferase of *Salvia*

Purification of malonyl transferase was conducted using red flowers 2,644 g of *Salvia splendens* as starting material. Flowers of *salvia* were collected in its entirety including calyces immediately before blossom, and were stored at −80° C. until use in experiments.

To 500 g of *salvia* flowers, polyvinylpolypyrrolidone (PvPP) 100 g, extraction buffer (100 mM potassium phosphate (pH 7.0), 30 mM 2-mercaptoethanol, 5 mM EDTA) 3 L and phenylmethylsulfonylfluoride (PMSF) of a final concentration 0.5 mM were added, and powdered with a HEAVY DUTY BLENDER (WARING). The solution containing the powdered material was centrifuged at 7,500×G for 20 minutes. Supernatant was filtered under reduced pressure (filter paper, Whatman 114) to obtain a crude enzyme solution. A crude enzyme solution of 10.4 L was obtained from flowers of 2,664 g.

Next, ammonium sulfate fractionation was conducted, and an enzyme was recovered as precipitation in 20% to 50% saturated ammonium sulfate fraction and dissolved in buffer A (100 mM potassium phosphate (pH 7.0), 30 mM 2-mercaptoethanol, 1 mM EDTA, 0.1 mM PMSF)(2920 ml). 280 ml of Octyl Sepharose Fast Flow (Amersham Pharmacia Biotech Co.) was added to this, and ammonium sulfate was slowly added to a final concentration of 30% saturation while the solution was slowly stirred. After adequate stirring, the solution was allowed to stand still overnight. After confirming that enzyme activity of malonyl transferase was not left in the supernatant liquid, the gel in the sludge was recovered by filtration under reduced pressure (filter paper, Whatman 114). The gel was extensively washed with buffer B (20 mM potassium phosphate (pH 7.0), 30 mM 2-mercaptoethanol, 20% saturated ammonium sulfate), while being filtered under reduced pressure.

280 ml of buffer C [20 mM potassium phosphate (pH 7.0), 15 mM 2-mercaptoethanol, 50% ethylene glycol, 0.1% 3-[(3-cholamidopropyl)dimethylammonio]-1-propanesulfonate (CHAPS)] was added to the gel, and after being gently stirred for 30 minutes, a malonyl transferase active fraction was recovered by filtration under reduced pressure. This elution operation with buffer C was repeated 10 times to collect an active fraction. After the active fraction was concentrated using Pellicon (Biomax 8K, MILLIPORE CORPORATION), and was desalted in buffer D (10 mM potassium phosphate (pH 7.0), 15 mM 2-mercaptoethanol, 0.03% TritonX-100), 155 ml of enzyme solution 1 was obtained.

MIMETIC Yellow 2 (Nacalai Tesque Co.) 100 ml was loaded to Econocolumn (φ1.0 cm×120 cm, Japan Bio Rad Laboratories Co.), and was equilibrated with buffer D. After the total amount of the enzyme solution 1 was applied and washed with buffer D, protein bound to the column was eluted using buffer E (20 mM potassium phosphate (pH 7.0), 30 mM 2-mercaptoethanol, 0.05% CHAPS). The active fraction was concentrated using Pellicon and ultrafiltration (YM-10, MILLIPORE CORPORATION), and 32 ml of enzyme solution 2 was obtained.

MIMETIC Red 3 (Nacalai Tesque Co.) 50 ml was loaded to Econocolumn (φ1.5 cm×30 cm, Japan Bio Rad Laboratories Co.), and was equilibrated with buffer F (5 mM potassium phosphate (pH 7.0), 15 mM 2-mercaptoethanol, 0.03% TritonX-100). After the total amount of enzyme solution 2 was applied and washed with buffer F, the proteins bound to the column were eluted using buffer G (5 mM potassium phosphate (pH 7.0), 30 mM 2-mercaptoethanol, 0.03% TritonX-100, 0.1 mM acetylCoA). After the active fraction was concentrated using Pellicon, ultrafiltration, and Centricon, it was desalted using buffer H (30 mM potassium phosphate (pH 7.0), 30 mM 2-mercaptoethanol, 0.03% TritonX-100), and 3 ml of enzyme solution 3 was obtained.

MIMETIC Red 3 (Nacalai Tesque Co.) 5 ml was loaded to Econocolumn (φ1.0 cm×10 cm, Japan Bio Rad Laboratories Co.), and was equilibrated with buffer F. After the total amount of the enzyme solution 3 was applied and washed with buffer F, the proteins bound to the column were eluted using buffer G. After the active fraction was concentrated using Centricon, 1.5 ml of enzyme solution 4 was obtained.

After a MonoQ5/5 column (Amersham Pharmacia Biotech Co.) was equilibrated with buffer G, the total amount of the enzyme solution 4 was applied at a flow rate of 0.05 ml/min and was washed with buffer F (flow rate 0.05 ml/min for 60 minutes). The proteins bound to the column were eluted using a 0 to 100% linear gradient (flow rate 0.05 ml/min, for 400 min) formed with buffer I (20 mM potassium phosphate (pH 7.0), 30 mM 2-mercaptoethanol, 0.03% TritonX-100, 1 mM NaCl), and after the active fraction was concentrated using Centricon, 0.8 ml of enzyme solution 5 was obtained.

After Phenyl Superose HR 5/5 (Amersham Pharmacia Biotech Co.) was equilibrated with buffer B, the enzyme solution 5 having ammonium sulfate added to a final concentration of 20% saturation was applied at a flow rate of 0.02 ml/min. After the column was washed with buffer B, the proteins bound to the column were eluted using a 0 to 100% linear gradient formed with buffer C (flow rate of 0.02 ml/min, for 500 minutes), and the active fraction was obtained.

Further, a preparative electrophoresis system (Bio Phoresis III, Atto Co.) was used for fractionation, and the obtained fraction of 3.2 ml of malonyl transferase was concentrated to 40 µl using ultrafiltration membrane concentration, with substituting with 0.02% SDS/75 mM Tris-HCl buffer (pH 8.8). Thereafter, final purification was performed using a reverse phase column (PorosR2H, Japan Perceptive Co.) HPLC. Separation was conducted under the condition of a linear concentration gradient in 0.1% TFA formed by an acetonitrile concentration from 8% to 80%, at a flow rate of 0.1 ml/min for 60 minutes, and monitoring absorption at 280 nm, only the peak fraction was recovered. Since the protein finally obtained turned out to be a single band of 47 kDa, it was determined that the molecular weight of the malonyl transferase was 47 kDa.

Example 4

Determination of Partial Amino Acid Sequences of the Malonyl Transferase of *Salvia*

2 pmol of trypsin (Promega Co.) was added to the protein that was recovered in Example 3 as a single band. The protein was digested at 37° C. for 30 hours, and determination of the structure of each peptide fragment was attempted. Solution digested by trypsin was separated using reverse phase HPLC (µRPC C2/C18, Amersham Pharmacia Biotech Co.) into each peptide fragment. Separation was conducted under 0.1% trifluoroacetic acid using a linear concentration gradient formed with acetonitrile concentration from 8% to 80% for 60 minutes at a flow rate of 0.1 ml/min, and, while monitoring absorption at 215 nm, only absorption peak fractions were collected.

Each peak fraction was concentrated and dried by speedback, and was dissolved in 30 μl of 37% acetonitrile and subjected to analysis using an amino acid sequencer (PSQ-1, Shimadzu Corporation). As a result, amino acid sequences of 12 peptides were obtained. The amino acid sequences are shown below.

MTT20: Tyr-Ala-Ala-Gly-Asp-Ser-Val-Pro-Val-Thr-Ile-Ala-Ala-Ser-Asn (SEQ ID NO: 7)
MTT21-1: Leu-Leu-Phe-Tyr-His-His-Pro-Ser-Ser-Lys (SEQ ID NO: 8)
MTT21-2: Ser-Gly-Asp-Lys-Ser-Asp-Glu-Asn-Ala-Pro-Glu-Leu-Phe-Ile-Ile-Pro-Ala-Asp-Ala (SEQ ID NO: 9)
MTT22-1: Met-Ala-Ala-Phe-Glu-Glu-Val-Phe (SEQ ID NO: 10)
MTT23: Trp-Leu-His-Tyr-His-Pro-Val (SEQ ID NO: 11)
MTT26: Gly-Ala-Glu-Asn-Trp-Met-Ser-Asp-Ile-Phe-Lys (SEQ ID NO: 12)
MTT27-2: Leu-Ala-Ala-Glu-Xaa-Gly-Phe-Ala-Val-Ala-Ala-Ala-Ala-Ile-Gly-Gly-Gly-Ile-Ile-Gly (SEQ ID NO: 13)
MTT28: Ser-Phe-Ile-Asn-Asp-Pro-Asn-Lys-Ile-Asp-Ala-Ile-Phe (SEQ ID NO: 14)
MTT141: Thr-Ala-Ser-Phe-Pro-Leu-Pro-Thr-Asn-Arg (SEQ ID NO: 15)
MTT141-2: Phe-Pro-Gln-Leu-Arg (SEQ ID NO: 16)
MT142: Ala-Asp-Phe-Gly-Trp-Gly-Lys (SEQ ID NO: 17)
MTT291: Asp-Ala-Asp-Gln-Phe-Tyr-Asp-Leu-Leu-Pro-Pro-Ile-Pro-Pro (SEQ ID NO: 18)

Example 5

Amplification of Gene Fragments Encoding Malonyl Transferase of *Salvia*

MT142 obtained in Example 4, the following primers were constructed.
MTT20-1: 5'-TA(T/C) GCI GCI GGI GA(T/C) TCI GTI CCI GT-3' (I: inosine) (SEQ ID NO: 19)
MTT20-3: 5'-GTI CCI GTI ACI AT(A/T/C) GCI GC-3' (SEQ ID NO: 20)
ATCRr2: 5'-(T/C)TT ICC CCA ICC (A/G)AA (A/G)TC IGC-3' (SEQ ID NO: 21)

PCR was carried out using cDNA prepared from *salvia* flowers as a template, with reactant solution having that following composition in a total amount of 100 μl; 1×TAKARA PCR buffer, 200 mM dNTPs, *salvia* cDNA 100 ng, MTT20-1 primer 1 pmol/μl, ATCRr2 primer 1 pmol/μl, TAKARA rTaq 2.5 units. Reaction was conducted at 96° C. for 1 minute, followed by 30 cycles with each cycle consisting of 1 minute at 96° C., 2 minutes at 42° C. and 3 minutes at 72° C., and further followed by 7 minutes at 72° C.

Nested PCR was carried out using this reaction product as a template, and using MTT20-3, ATCRr2 primers, with reactant solution of the same composition as described above. Reaction was conducted at 96° C. for 1 minute, followed by 30 cycles with each cycle consisting of 1 minute at 96° C., 2 minutes at 50° C. and 3 minutes at 72° C., and further followed by 7 minutes at 72° C. The PCR product obtained in this manner was subjected to subcloning, and its sequence was determined. As a result, in the deduced amino acid sequence of the reaction product of about 900 bp, partial amino acid sequences MTT141, MTT26, MTT27-2 (SEQ ID NO: 15, 12 and 13) beside with those used for design of primers were found. Thus, it was evident that the reaction product was a gene fragment encoding a purified protein.

Example 6

Isolation of cDNA Encoding the Malonyl Transferase of *Salvia*

A cDNA library derived from flowers of *Salvia guaranitica* was constructed using the λZAP II directional cDNA synthesis kit of Stratagene Co. in accordance with the method recommended by the manufacturer of the kit. About 200,000 clones of this library were screened using the washing condition (5×SSC, 0.1% SDS, 37° C.) with the DNA fragment of 889 bp obtained in Example 5 as a probe, and 10 clones were finally obtained as positive clones. These clones were classified into three kinds of groups, and the longest clones in these group are named as SgMaT1, SgMaT1', and SgMaT2, respectively. Screening of the library was conducted in accordance with known methods (for example, Fujiwara et al., 1998, Plant J. 16, 421).

SgMaT1 and SgMaT1' are 1419 bp and 1471 bp, respectively, and both lacked initiation methionine. Since SgMaT1 and SgMaT1' exhibit an identity of 98% at amino acid level, they were considered as an allelic gene encoding the same enzyme. In the deduced amino acid sequence of SgMaT1, all the partial amino acid sequences of purified malonyl transferase determined in Example 4 were confirmed, although some are partially different. The partial difference is probably due to the difference of species of *salvia* used.

From these results, it became evident that SgMaT1 and SgMaT1' genes encode an enzyme for transferring a malonyl group to a glycosyl group at the 5-position of anthocyanins. SgMaT2 has a cDNA of 1530 bp, which includes an open reading frame of 1260 bp encoding the full length. At the amino acid level, SgMaT1 exhibited 52% identify with SgMaT2. All of these genes exhibited a identity of 37 to 47% with acyl transferases of other plants.

In gentian, acyl transferases having different functions show identify of only 35 to 40%, even in the same varieties (Yonekura-Sakakibara et al., 2000, Plant Cell Physiol. 41: 495–502). Therefore, identity of 55% between SgMaT1 and SgMaT2 suggests, although the fact that the two genes are derived from the same variety is allowed for, that SgMaT1 and SgMaT2 are similar in function, and that SgMaT2 also catalyzes the reaction of transferring a malonyl group to anthocyanins. The nucleotide sequences of SgMaT1, SgMaT1', and SgMaT2 are shown in SEQ ID NO: 1, 3, and 5, respectively, and the amino acid sequences deduced from these nucleotide sequences are shown in SEQ ID NO: 2, 4, and 6, respectively.

Example 7

Confirmation of Enzyme Activity of the Malonyl Transferase in *Escherichia coli*

A single colony of *Escherichia coli* having plasmid pSgMaT1 (including SgMaT1 gene at EcoRI, XhoI sites of pBluescriptSK⁻ (Stratagene), and capable of expressing an SgMaT1 gene product as a fusion protein with lac Z protein by addition of isopropyl-beta-thiogalactoside (IPTG)) introduced, was inoculated to LB medium containing ampicilin to a final concentration of 50 mg/L, and was precultured overnight while being shaked at 37° C. The preculture (2 ml) was inoculated to LB medium of 100 ml containing ampicilin, and was incubated at 30° C. until absorbance at 600 nm became 0.5. Then, IPTG was added to the culture medium to a final concentration of 1 mM. The culture was further maintained at 30° C. for 9 hours after the addition of IPTG, and then was collected. The collected cells were suspended in a buffer (0.1 M KPB, pH 7.0, 30 mM 2-mercaptoethanol, 1 mM EDTA, 0.1 mM PMSF, 0.1% TritonX-100), and disrupted by ultrasonic treatment while cooled on ice.

Enzyme activity was measured using a supernatant (soluble fraction) obtained after centrifuging. *Escherichia coli* containing only pBluescriptSK⁻ was processed in the same manner as control. Measurement of activity was conducted using shisonin as a substrate in accordance with Example 2.

In the reaction product from the reaction using the pSgMaT1 gene expression product, malonyl-shisonin was detected (Rt 12.2 minutes) in addition to shisonin (Rt 9.7 minutes), while only shisonin was detected in control. It was confirmed from this that the SgMaT1 gene encodes an enzyme having activity of transferring the malonyl group.

Example 8

Isolation of cDNA Encoding Malonyl Transferase Derived from *Salvia* (2)

A cDNA library of flower petals of *salvia* (*Salvia splendens*) was constructed using a ZAP-cDNA Synthesis Kit (Strategene Co.) with λZAP II (Strategene Co.) as a vector, in accordance with the method recommended by the manufacturer. Using SgMaT1 obtained in Example 6 as a probe, screening was carried out by the method described in Example 6. The clone with the longest cDNA was denoted by SsMaT1. This nucleotide sequence is shown in SEQ ID NO: 22, and the amino acid sequence deduced from this nucleotide sequence is shown in SEQ ID NO: 23. Considering the sequence, this cDNA is not considered to be a full-length cDNA.

SsMaT1 exhibited 92% identity with SgMat1, and 52% identity with SgMaT2 at the amino acid level.

Similarly, the same library was screened using SgMaT2 as a probe, and SsMaT2 was obtained. This nucleotide sequence is shown in SEQ ID NO: 24, and the amino acid sequence deduced from this nucleotide sequence is shown in SEQ ID NO: 25.

SsMaT2 exhibited 53% identity with SgMat1, 96% identity with SgMaT2, and 52% identify with SsMaT1 in amino acid level.

Example 9

Isolation of cDNA Encoding the Malonyl Transferase Derived from *Perilla*

Young red leaves were collected from *perilla* (*Perilla frutescens*), and starting from this material, a cDNA library was constructed using a ZAP-cDNA Synthesis Kit (Strategene Co.) with λZAP II (Strategene Co.) as a vector, in accordance with the method recommended by the manufacturer. As in Example 8, this library was screened using SgMaT1 as a probe, and the clone having the longest cDNA among obtained clones was denoted by PfMaT1. The nucleotide sequence of PfMaT1 is shown in SEQ ID NO: 26, and the amino acid sequence deduced from the nucleotide sequence is shown in SEQ ID NO: 27.

PfMaT1 exhibited 67% identity with SgMaT1, 57% identity with SgMaT2, 65% identity with SsMaT1, and 57% identity with SsMaT2 in amino acid level.

Example 10

Isolation of cDNA Encoding the Malonyl Transferase Derived from Lavender

A cDNA library of lavender (*Lavendula angustifolia*) was constructed using a ZAP-cDNA Synthesis Kit (Strategene Co.) with λZAP II (Strategene Co.) as a vector, in accordance with the method recommended by the manufacturer. Using SgMaT2 obtained in Example 6 as a probe, screening was carried out by the method as described in Example 6, and LnMaT2 was obtained. This nucleotide sequence is shown in SEQ ID NO: 28, and the amino acid sequence deduced from this nucleotide sequence is shown in SEQ ID NO: 29.

LnMaT2 exhibited 53% identity with SgMaT1, 65% identity with SgMaT2, 51% identity with SsMaT1, 64% identity with SsMaT2, and 56% identity with PfMaT1 in amino acid level.

Example 11

Expression of *S. splendens* MaT1

A primer for introducing a BamHI site at the 5'-end of the SsMaT1 gene obtained in Example 8 (Primer #1: 5'-GGATCC ATC GAG GGA CGC ATG ACA ACA ACA ACA AC-3' (SEQ ID NO: 30)), a primer for introducing a BamHI site at the 3'-end of the SsMaT1 gene (Primer #2: 5'-GGATCC TTA CAA TGG TTC GAC GAG CGC GGG AGA-3' (SEQ ID NO: 31)), and a primer for deleting the BamHI site in the SsMaT1 gene (Primer #3: 5'-GGACCCG CCG ATA CCG GAA AAT TAC TTC-3' (SEQ ID NO: 32)) were synthesized. The primer #1 was designed such that a Factor Xa cleavage site (Ile-Glu-Gly-Arg) is encoded just before the SsMaT1 initiation codon, methionine.

A first PCR reaction was carried out using Primer #2 and Primer #3 with the plasmid (pBK-CMV-SsMaT1) having SsMaT1 cDNA introduced at multi-cloning sites (EcoRI, XhoI) of pBK-CMV phagemid vector (Toyobo Co.) as a template (composition of reactant: pBK-CMV-SsMaT1 100 ng, 1×pfu buffer (Stratagene Co.), 200 µM dNTPs, 1 µM Primer #2, 1 µM Primer #3, 2.5 U pfu polymerase (Stratagene Co.); reaction condition: 96° C. 2 minutes, (96° C. 1 minute, 70° C. 1 minute, 72° C. 3 minutes) ×30 cycles, 72° C. 7 minutes), and a PCR product (about 500 bp) was obtained.

Using the double strand DNA fragment of SsMaT1 obtained as the first PCR product and Primer #1, a second PCR reaction was carried out (composition of reactant: pBK-CMV-SsMaT1 100 ng, 1×pfu buffer, 200 µM dNTPs, 1 µM Primer #1, the first PCR product 100 ng, 2.5 U pfu DNA polymerase (Stratagene Co.); reaction conditions: 96° C. 7 minutes, (96° C. for 2 minutes, 70° C. for 1 minute, 72° C. for 7 minutes) ×30 cycles, 72° C. for 10 minutes).

The second PCR product was subjected to A-tail addition (the second PCR product 100 ng, 1×ExTaq buffer, 2 mM dATP, TAKARA ExTaq; 70° C., 30 minutes), and was cloned to pCR2.1-TOPO vector (Clonetech Co.). As a result, a plasmid for inserting a full-length SsMaT1 was obtained (pCR2.1-SsMat1). Using a DNA sequencer, it was confirmed that an incorrect nucleotide was taken into the DNA sequence of the SsMaT1 gene due to the PCR operation.

The pCR2.1-SsMaT1 was completely digested with BamHI, and a produced DNA fragment of about 1400 bp was recovered. This DNA fragment was subcloned to the BamHI site of *Escherichia coli* expression vector pQE-30 (QIAGEN Co.), and was denoted by pQE-30Xa-SsMaT1.

Expression of SsMaT1 in *Escherichia coli* containing pQE-30Xa-SsMaT1 was conducted in accordance with the method described in Example 7. Measurement of enzyme activity was conducted in accordance with the method described in Example 2.

Extract from *Escherichia coli* expressing the SsMaT1 gene was used to measure enzyme activity, and it was confirmed that malonyl-shisonin was produced in addition to shisonin. Thus, it was confirmed that the SsMaT1 gene encodes a protein having activity for transferring a malonyl group to a glycosyl group at 5-position of flavonoids.

When acetyl CoA, methylmalonyl CoA, or succinyl CoA was used in place of malonyl CoA as a substrate, a new peak in addition to shisonin was observed in column chromatography using HPLC, indicating that SsMaT1 has activity for transferring these substrates to shisonin.

Example 12

Expression of *P. frutescens* MaT1

As in Example 7, using a plasmid constructed such that the PfMaT1 gene obtained in Example 9 can be expressed as a fusion protein fused with LacZ protein, the PfMaT1 gene was expressed in *Escherichia coli* as in Example 7, and enzyme activity was measured. Measurement of enzyme activity was conducted in accordance with the method described in Example 2.

An extract from *Escherichia coli* expressing the PfMaT1 gene was used to measure enzyme activity, and it was confirmed that malonyl-shisonin was produced in addition to shisonin. Thus, it was confirmed that the PfMaT1 gene encodes a protein having activity for transferring a malonyl group to a glycosyl group at 5-position of flavonoids.

INDUSTRIAL APPLICABILITY

It has been made evident for the first time by the present invention that an aliphatic acyl transferase is involved in the control of flower colours. Flower colour can be altered by expressing this protein in flower petals for modifying anthocyanins. As an aliphatic acyl transferase, any gene which encodes a protein having the same enzyme activity in other organisms may be used in addition to the above-described genes derived from *salvia*, *perilla* plant, and lavender.

The invention claimed is:

1. An isolated or synthesized gene encoding a protein which comprises an amino acid sequence exhibiting at least 65% identity with an amino acid sequence selected from the group consisting of SEQ ID NO: 2, 23, and 27 and wherein the protein has an activity to transfer a malonyl group to a glycosyl group at the 5-position of anthocyanins.

2. The isolated or synthesized gene according to claim 1, wherein the gene encodes a protein which comprises an amino acid sequence selected from the group consisting of SEQ ID NO: 2, 23, and 27.

3. The isolated or synthesized gene according to claim 1, wherein the gene encodes a protein which comprises an amino acid sequence exhibiting identity of at least 80% with an amino acid sequence selected from the group consisting of SEQ ID NO: 2, 23, and 27.

4. A vector comprising a gene according to claim 1.

5. A host transformed by a vector according to claim 4.

6. A transgenic plant comprising a gene according to claim 1 introduced therein, or offspring or tissue thereof comprising said gene.

7. A cut flower of the transgenic plant according to claim 6 or the offspring thereof comprising said gene.

8. A method for altering the colour of flowers by introducing a gene according to claim 1 into the genome of a plant containing anthocyanins and causing constitutive or tissue-specific expression of said gene in the plant.

9. A method for blueing the colour of flowers by introducing a gene according to claim 1 into the genome of a plant containing anthocyanins and causing constitutive or tissue-specific expression of said gene in the plant.

* * * * *